United States Patent [19]
Konishi et al.

[11] Patent Number: 6,127,337
[45] Date of Patent: Oct. 3, 2000

[54] BIVALENT THROMBIN INHIBITORS

[75] Inventors: Yasuo Konishi, Kirkland, Canada; Zbigniew Szewczuk, Wroclaw, Poland; Yuko Tsuda, Akashi, Japan

[73] Assignee: National Research Council of Canada, Ottawa, Canada

[21] Appl. No.: 08/636,698

[22] PCT Filed: Oct. 25, 1994

[86] PCT No.: PCT/CA94/00585

§ 371 Date: Jun. 28, 1996

§ 102(e) Date: Jun. 28, 1996

[87] PCT Pub. No.: WO95/11921

PCT Pub. Date: May 4, 1995

[30] Foreign Application Priority Data

Oct. 25, 1993 [GB] United Kingdom .................... 9321951
Jun. 24, 1994 [GB] United Kingdom .................... 9412707

[51] Int. Cl.[7] .............................. A61K 38/03; C07K 7/00
[52] U.S. Cl. .................................. 514/13; 514/14; 514/15; 514/16; 530/326; 530/327; 530/328; 530/329
[58] Field of Search .................................. 514/13–15, 16, 514/822; 530/326–328, 329

[56] References Cited

U.S. PATENT DOCUMENTS 3,978,045  8/1976  Okamoto et al. .................... 260/239 B
4,173,630  11/1979  Okamoto et al. ........................ 424/177
5,196,404  3/1993  Maraganore et al. ..................... 514/13

OTHER PUBLICATIONS

Brandstetter et al., J. Mol. Biol. (1992) 226 1085–99.
Szewczuk et al. Biochem (1993) 32 3396–3404.
Krstenansky et al., Titromb. & Hafm. 63(2) 208–14 (1990).

*Primary Examiner*—Bennett Celsa
*Attorney, Agent, or Firm*—J. Wayne Anderson

[57] ABSTRACT

Hirudin is the most potent and specific thrombin inhibitor and is derived from the medicinal leech. It is reported to inhibit thrombin with an equilibrium dissociation constant ($K_i$) value of $2.2 \times 10^{-14}$ M. synthetic thrombin inhibitors have been designed based on the hirudin sequence but with a dramatically reduced size. The bulky active site inhibitor segment, hirudin$^{1-48}$, has been substituted by small non-substrate type active site inhibitors of thrombin, e.g., dansyl-Arg-(D-pipecolic acid). The linker segment has also been modified using a combination of ω-amino acids to reduce the molecular weight but retaining sufficient length to span the two principal binding domains. Among the inhibitors designed, dansyl-Arg-(D-pipecolic acid)-(12-aminododecanoic acid)-4-aminobutyric acid)-Asp-Tyr-Glu-Pro-Ile-Pro-Glu-Glu-Ala-(L-β-cyclohexylalamine)-(D-Glu)-OH (SEQ ID NO:45) showed the highest affinity and displays a competitive-type inhibition. The incorporation of the non-substrate type active site inhibitor segment and the linker of ω-amino acids into the bivalent thrombin inhibitors not only improved in vitro thrombin inhibitory activity to the pM level, overcame proteolytic susceptibility at the level of the "normal" scissile bond and confered high in vivo activity.

12 Claims, 5 Drawing Sheets

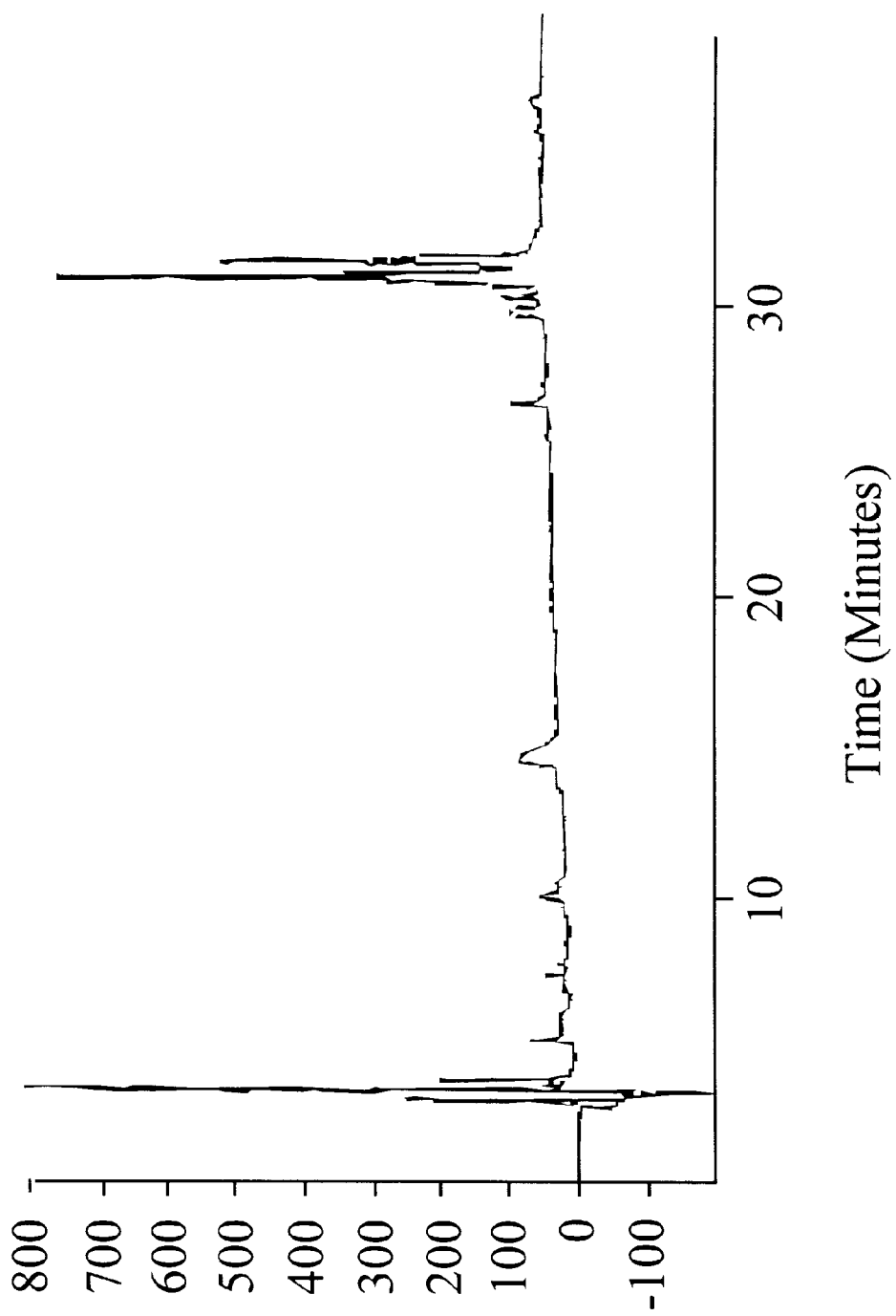

BIVALENT THROMBIN INHIBITORS

This application is a 371 of PCT/CA94/00585 Oct. 25, 1994.

BACKGROUND OF THE INVENTION

Thrombin plays a central role in the coagulation cascade of higher animals. The primary function of thrombin is to activate fibrinogen to fibrin and generate an insoluble fibrin clot. It also serves regulatory functions in coagulopathy by activating several participating cofactors and proteases such as factor V, factor VIII, factor XIII and protein C. In a pathologic state, thrombin promotes coagulopathy, activates platelets and causes secretion of granular substances that exacerbate the condition. Thrombin's interaction with endothelial cells, smooth muscle cells, fibroblasts, and monocytes/macrophages contribute further to the inflammatory process in thrombotic events. An acute blockage of a coronary artery by a thrombus causes a myocardial infarction. In its early stages, the condition may be alleviated with thrombolytic therapy. However, typical thrombolysis with tissue plasminogen activator, urokinase or streptokinase is problematic. Acute thrombotic reocclusion often occurs after initial successful thrombolysis using these agents. Although the mechanism of reocclusion has not been clearly elucidated, thrombus-bound thrombin may contribute to this problem. Potent and specific agents that neutralize thrombus-bound thrombin would be desirable.

Thrombin is a member of the trypsin family of serine proteases. In addition to the catalytic triad (Asp 102, His 57 and Ser 195) a feature common to the active site of all serine proteases, asp 189 in the primary substrate binding site (S1) of the trypsin family plays an important role in the recognition and binding of substrates and inhibitors.

A natural anticoagulant, heparin inhibits thrombin through a mechanism requiring a heparin-antithrombin III compounds. Heparin is known to be poorly accessible to thrombus-bound thrombin. Furthermore, heparin often causes bleeding when used therapeutically and is unable to prevent the occlusive complications in atherosclerotic vascular diseases or reocclusion following successful thrombolysis.

Another agent known to be effective for the inhibition of thrombus-bound thrombin is hirudin. Hirudin is produced by the salivary glands of the European medicinal leech Hirudo medicinalis and is a small protein of 65 amino acid residues. It has several potential advantages over other antithrombotics. It is the most potent and specific thrombin inhibitor known having a $K_i$ value of $2.2 \times 10^{-14}$ M. Hirudin blocks the active site (AS) and the fibrinogen recognition exosite (FRE) of thrombin simultaneously. Hirudin also inhibits thrombus-bound thrombin as well as circulating thrombin and it has a long half-life of 30–60 minutes when given intravenously or subcutaneously, depending on the species. Hirudin has very weak antigenicity, and it has no reported acute side effects following intravenous or subcutaneous administration.

Synthetic thrombin inhibitors based on the hirudin sequence offer an advantage over native hirudin. They mimic the distinctive mechanism of hirudin and are more readily available through chemical synthesis. The crystal structure of the human a-thrombin/hirudin complex reveals that hirudin interacts with the enzyme through an active site inhibitor domain (hirudin[1-48]), a FRE inhibitor segment (hirudin[55-65]), and a linker segment (hirudin[49-54]) which connects these binding components.

The bulky active site inhibitor segment, hirudin [1-48], is sufficiently large and serves to obstruct the enzyme surface. This action has been shown to be simulated when hirudin [1-48] is replaced by a small active site inhibitor segment, D-Phe-Pro-Arg-Pro, with some loss in inhibitory potency (Maraganore, J. M., Bourdon, P., Jablonsky, J., Ramachandran, K. L., & Fenton, J. W. 11 (1990) *Biochemistry* 29, 7095–7101; DiMaio, J., Gibbs, B., Munn, D., Lefebvre, J. Ni, F., and Konishi, Y., (1990) *J.Biol.Chem* 265, 21698–21703; Bourdon, P., Jablonski, J. -A., Chao, B. H., and Maraganore, J. M., 9, (1991) (*FEBS Lett.* 294, 163–166).

Investigators have focused on the use of D-Phe-Pro-Arg-Pro or its analog in the design of active site inhibitors. The crystal structure of D-Phe-Pro-Arg chloromethylketone (PPACK)-thrombin suggested that the D-Phe-Pro-Arg-Pro in bivalent inhibitors bind to the thrombin active site in a substrate binding mode, wherein Arg-X is the scissile peptide bond. The active site inhibitor segment, D-Phe-Pro-Arg-Pro, of the bivalent inhibitors is known to be hydrolyzed slowly by thrombin (DiMaio, J., Gibbs, B., Munn, D., Lefebvre, J., Ni, F. and Konishi, Y. (1990) *J. Biol. Chem.* 265, 21698–21703; Witting, J. I., Bourdon, P., Maraganore, J. M., and Fenton, J. W., II (1992) *BioChem. J.* 287, 663–664). The amino acids (D-Phe)-Pro-Arg comprised in the substrate type inhibitor (D-Phe)-Pro-Arg-Pro respectively bind to the S3, S2 and S1 subsites of thrombin.

Hirulog-8™ is a bivalent thrombin inhibitor composed of the substrate type inhibitor (D-Phe)-Pro-Arg-Pro, and the native sequence of the hirudin exosite segment 52–65 both linked through a suitable linker (Maraganore et al. U.S. Pat. No. 5,196,404). Since the structure of those thrombin inhibitor is very similar to the structure of hirudin, the interactions of the substrate type active site inhibitor with thrombin are the same as the interactions between the active site of hirudin and thrombin. In addition, it has been shown that the portion (D-Phe)-Pro-Arg-CO can be used in a bivalent thrombin inhibitor (DiMaio et al. International publication WO 91/19734). Apparently, the use of the acetyl function at the scissile position gives more resistance to enzyme degradation without affecting the inhibitory activity. The scissile position in a substrate is a position that is recognised by the enzyme and where the hydrolysis takes place. It is therefore advantageous to eliminate or to modify the scissile position in order to give to more resistance to enzyme degradation. Since the structure of the two classes of bivalent thrombin inhibitors mentioned above are similar to the structure of hirudin, their synthesis is difficult, cumbersome, uses dangerous chemicals and affords low yields of the desired compounds. There is therefore a need for other thrombin inhibitors that would combine high inhibiting activity, enzyme resistance and affordable synthesis.

Besides substrate-type inhibitors, nonsubstrate type inhibitors could be designed to block the active site of thrombin without being cleaved. Examples of these may be derived from arginine and benzamidine to give, for example, (2R,4R)-4-methyl-1-[N$^\alpha$-(3-methyl-1,2,3,4-tetrahydro-8-quinolinesulphonyl)-L-arginyl]-2-piperidine carboxylic acid (MD-805), N$^\alpha$-(4-toluene-sulphonyl)-D,L-amidinophenylalanyl-piperidine (TAPAP), and N$^\alpha$-(2-naphthyl-sulphonyl-glycyl)-D-L,p-amidinophenylalanyl-piperidine (NAPAP). These active-site directed synthetic inhibitors have a short half-life of less than several minutes in the circulation. This activity is not of sufficient duration to be effective against the continuous production of thrombin by the patient or against the effect of liberated thrombus bound-thrombin. The characteristic sequence of these compounds starting from the N-terminus is an aromatic group, arginyl or benzamidyl, and piperidide or its analogs. In contrast to hirudin-based sequences, these moieties would be expected to occupy the S3, S1 and S2 subsites of the thrombin active site, respectively.

This mechanism of interaction contrasts with the mode of interaction manifest by substrate-like inhibitors. Accordingly, incorporation of a non-substrate type active site inhibitor into the bivalent inhibitor may have advantages over the substrate like counterparts. For example, a linker attached to the P2 residue piperidide or its analogs could eliminate a labile peptide bond that normally spans the scissile position. The potency of the bivalent inhibitor might be improved because of the higher affinity of the non-substrate type active site-directed segment.

It would be desirable to develop a shortened thrombin inhibitor of the hirudin type. Such a shortened sequence would be easier to synthesize and cheaper to produce. It would have a drastically shortened linear sequence and would be less subject to enzymatic degradation in a mammal.

It has been found that such a hirudin-like agent would more likely work well if it blocked both the enzyme activity site of thrombin and the fibrinogen-recognition exosite. It would be even more desirable if both these sequences were chemically connected so as to have both abilities in one compound.

It has been previously reported that the combination of dansyl or dansyl analogues, arginine or benzamidine, and pipecolic acid attaches to the thrombin enzyme activity site. But it has been shown that such activity is weak and not pharmacologically useful (James C. Powers and Chih-Min Kam, Thrombin: Structure and Function, Chapter 4, (1992), Lawrence J.Berliner. Plenum Press, New York).

The invention seeks to provide improved bivalent inhibitors having increased potency and proteolytic stability comprising non-substrate type active site inhibitor segment. Abbreviations. The following abbreviations have been used in the specification: Abu, γ-aminobutyric acid; Ac, acetyl; Aca, ε-aminocaproic acid; Aca*, 8-aminocapylic acid; Acha, 1-aminocyclohexane-carboxylic acid; Ada, 12-aminododecanoic acid; AMC, 7-amino-4-methylcoumarin; Aua, 11-aminoundecanoic acid; Ava, δ-aminovaleric acid; Bal, β-alanine; Boc, tert-butyloxycarbonyl; BrBzs, 4-bromobenzenesulfonyl; Bzs, benzene sulfonyl; Cha, β-cyclohexylalanine; Fmoc, 9-fluorenylmethoxycarbonyl; FRE, fibrinogen recognition exo site; HPLC, high performance liquid chromatography; MD805, (2R,4R)-4-methyl-1-[N$^\alpha$-(3-methyl-1,2,3,4-tetrahydro-8-quinolinesulphonyl-glycyl)-L-arginyl]-2-piperidine carboxylic acid; NAPAP, N$^\alpha$(2-naphtyl-sulphonyl)-D,L-p-amidinophenylalanyl-piperidide; Nas, naphtylsulfonyl; Nle, norleucine; 3-TAPAP, N$^\alpha$-(4-toluene-sulphonyl)-D,L-p-amidinophenylalanyl-piperidide; OBzl, benzylester; Pip, pipecolic acid; PPACK, D-Phe-Pro-Arg chloromethylketone; tBbs, 4-tert-butylbenzenesulfonyl; Tic, 1,2,3,4-tetrahydroisoquinoline-3-carboxylic acid; TipBs, 2,4,6 triisopropylbenzenesulfonyl; TFA, trifluoroacetic acid; Tos, tosyl; Tris, 2-amino-2-(hydroxymethyl)-1,3-propanediol. All amino acid residues are L-configuration unless otherwise indicated. $IC_{50}$ is defined as the inhibitor concentration required to double the clotting time relative to the control; means of three determinants ±SEM.

FIGURES AND TABLES

FIGS. 1a and 1b. Dixon plot of the hyperbolic and slow competitive inhibition of human α-thrombin (0.033 NIH unit/mL) by (A) P448 ($K_i$=17.0±4.2 pM) and (B) P498 ($K_i$=131±22 pM), respectively. The fluorogenic assay was performed using Tos-Gly-Pro-Arg-AMC ($K_s$=3.5 μM and $V_{max}$=1.4 μM/min) as a substrate at pH 7.8 and 25° C. The amount of product, 7-amino-4-methylcoumarin, is plotted at a substrate concentration of (A) 40 μM or (B) 4 μM and as a function of various concentrations of inhibitors as a function of time.

FIGS. 2a–2c. HPLC profile of the compounds of this invention, more specifically of P448 (A) after 6 hours of incubation with human thrombin, (B) after 3 hours of incubation with human plasma proteases, and (C) after 60 minutes of incubation with kidney membrane homogenates. The peaks at around 3.8 and 33.5 minutes and small peaks at 7.1, 10.6, 27.8, 28.4, 36.5 and 37.0 minutes in (B) are due to the proteins in human plasma. The details of the digestions are described under Experimental Procedures of Example 2.

Table I shows $K_i$ and $IC_{50}$ values for several thrombin active site directed inhibitors. Their inhibition was analyzed using the method in Segel 1975.

Table II shows the $K_i$ activity values for bivalent inhibitors with various active site inhibitor segments. The exosite segment in all of the examples corresponds to the amino acid sequence of the exosite on natural hirudin.

Table III shows the effect of variations within the linker segment Z (the spacer function) on the $K_i$ and $IC_{50}$ values of the resulting thrombin inhibitors.

Table IV shows the effect of the variations within the fibrinogen recognition exosite inhibitor segment, G-$X_2$-$G_1$-Q-$X_3$-$R_2$, (SEQ ID NO:1) on the $K_i$ values of the resulting thrombin inhibitors.

Table V shows the effect of the variations within the active site segment, the linker segment Z and the fibrinogen recognition exosite inhibitor segment, G-$X_2$-$G_1$-Q-$X_3$-$R_2$, (SEQ ID NO:1) on the $K_i$ values and $IC_{50}$ of the resulting thrombin inhibitors.

Table VI shows the effect of the variations within the active site segment, the linker segment Z and the fibrinogen recognition exosite inhibitor segment, G-$X_2$-$G_1$-Q-$X_3$-$R_2$ (SEQ ID NO:1)in the carotid injury-induced thrombosis assay.

SUMMARY OF THE INVENTION

We have made the surprising discovery that the combination dansyl-arginyl-pipecolic acid and its derivatives have a very strong hirudin-like activity when combined with the natural hirudin exosite oligopeptide sequence—or an analogue thereof—via a suitable linker sequence. The surprising properties of the compounds of this invention reside in the fact that unlike other known bivalent inhibitor, the active site portion of the compound of this invention is a non-substrate-type inhibitor which binds to thrombin in a different S3,S1,S2 pattern. It was therefore surprising that the non-substrate-type active site inhibitor was able to conserve its inhibiting properties in a bivalent form. Furthermore, unlike other known bivalent inhibitor, where the choice of the linker was arbitrary and simply had to be the same as the linker portion of naturally occurring hirudin, the length of the linker of the compounds of the present invention had to be modified because of the different binding pattern of the active site inhibitor. The compounds of the invention are at least 1000 times more active than the dansyl-arginyl-pipecolic acid sequence alone.

Surprisingly, the dansylated arginyl pipecolamide compounds acquire dramatically enhanced thrombin specificity when compoundd with an exosite recognizing sequence via a suitable linker. The resulting compounds of this invention demonstrate a substantial advantage compared to the use of an uncompleted active site compound. Furthermore the compounds of this invention show inhibitory activity comparable to hirudin.

The compounds of this invention are also stable to enzyme degradation. There is therefore a concrete benefit in using the compounds of this invention as thrombin inhibitors.

The compounds of this invention are defined by formula (I) or pharmaceutically acceptable salts thereof:

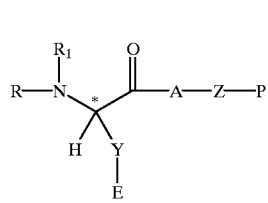

(I)

wherein, R is selected from the group consisting of:

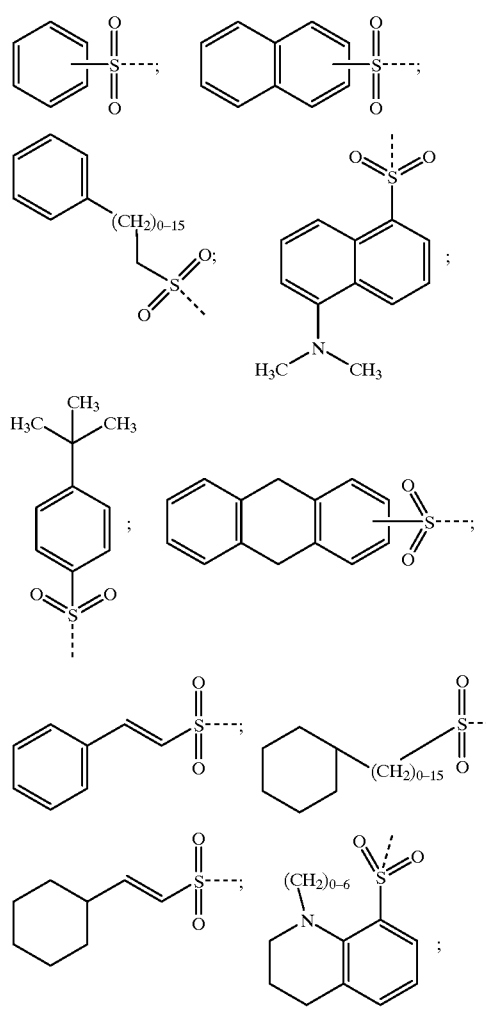

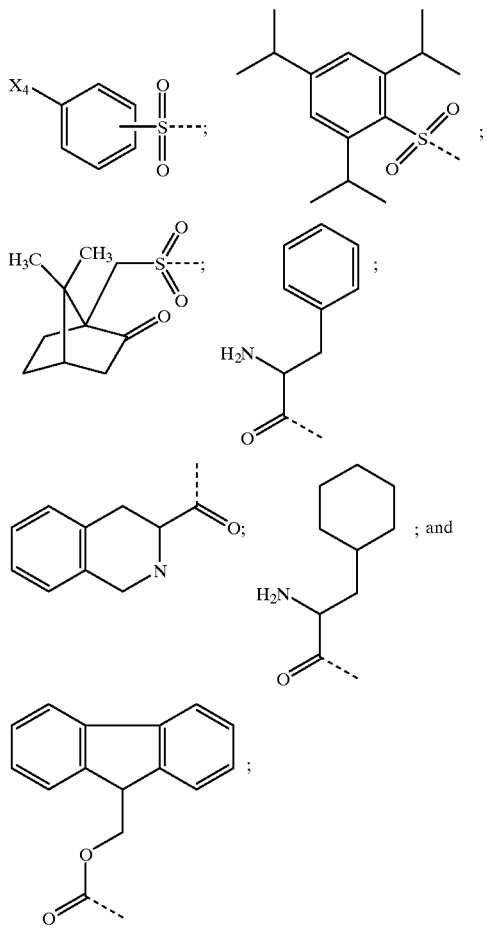

wherein $X_4$ is an halogen (e.g., Cl, Br, or F).

In the compounds of formula (I) $R_1$ is selected from the group consisting of hydrogen, alkyl, alkoxyalkyl, aryl and aralkyl.

Y is selected from the group consisting of alkyl, aryl, and aralkyl.

E is guanidyl, amidino or hydrogen.

A is selected from the group consisting of imino acid residue of either D or L configuration which may be substituted with an alkyl group or an aralkyl group; and hydrophobic amino acid residue.

Z is a divalent straight-chained saturated or unsaturated linker spanning at least 12 atoms linearly.

P is a peptide of at least 6 amino acid or imino acid residues selected from any fibrinogen recognition exosite portion of a hirudin molecule or analogue thereof.

As used in this application, the term <<alkyl>> represents a saturated or unsaturated; substituted (by a halogen, hydroxyl or $C_{6-20}$ aryl) or unsubstituted; straight chain, branched chain, or cyclic hydrocarbon moiety having 1 to 30 carbon atoms and preferably from 1 to 6 carbon atoms this chain or cyclic hydrocarbon moiety may be interrupted by at least one heteroatom such as N, O or S.

The term <<aryl>> represents a carbocyclic moiety which may be substituted by at least one heteroatom (e.g., N, O or S) and containing one benzenoid-type ring preferably containing from 6 to 15 carbon atoms (e.g., phenyl and naphthyl), this carbocyclic moiety may be interrupted by at least one heteroatom such as N, O or S.

The term <<aralkyl>> represents an aryl group attached to the adjacent atom by an alkyl group (e.g., benzyl), preferably containing from 6 to 30 carbon atoms.

The term <<alkoxyalkyl>> represents a substituted or unsubstituted alkyl group containing from 1 to 30 carbon atoms and preferably from 1 to 6 carbon atoms, wherein the alkyl group is covalently bonded to an adjacent element through an oxygen atom (e.g., methoxy and ethoxy).

Unless specified otherwise, the term "amino acid" used herein includes naturally-occurring amino acids as well as non natural analogs as those commonly used by those skilled in the art of chemical synthesis and peptide chemistry. A list of non natural amino acids may be found in "The Peptides", vol. 5, 1983, Academic Press, Chapter 6 by D. C. Roberts and F. Vellaccio. It is to be noted that unless indicated otherwise, the amino acids used in the context of the present invention are those in the L-configuration.

By a hydrophobic amino acid is usually meant an amino acid that bears an alkyl or aryl group attached to the α-carbon atom. Thus glycine, which has no such group attached to the α-carbon atom is not a hydrophobic amino acid. The alkyl or aryl group can be substituted, provided that the substituent or substituents present do not detract from the overall hydrophobic character of the amino acid. Water-solubilyzing such as OH, COOH and $NH_2$ are preferably to be avoided. Examples of hydrophobic amino acids include natural amino acid residues such as alanine; histidine; isoleucine; leucine; phenylalanine; tryptophane; tyrosine; and unnatural amino acid such as those described in "The Peptides", vol. 5, 1983, Academic Press, Chapter 6 by D. C. Roberts and F. Vellaccio. For example, one may cite cyclohexylalanine; 1-aminocyclohexane-carboxylic acid; and subphenylalanine. Subphenylalanine represents the phenylalanine residue bearing substituents on the aromatic ring. Common substituents used by those skilled in the art of amino acid chemistry are halogens (fluoride, bromide, and chloride), electron withdrawing group ($NO_2$) or lower alkyl or aryl substituents in the 2, 3, or 4 position.

By acidic amino acid is usually meant an amino acid that bears at least one water-solubilizing substituent attached to the α-carbon atom. Said water-solubilizing substituent is independently selected from the group consisting of alkoxy; carboxylic; hydroxyl; $NH_2$; and carboxyalkyl. Thus glycine, which has no such group attached to the α-carbon atom, is not an acidic amino acid. Example of acidic amino acids includes natural amino acids residues such as serine; threonine; cysteine; tyrosine; asparagine; glutamine; aspartic acid; glutamic acid; lysine; and unnatural amino acids such as those described in "The Peptides", vol. 5, 1983, Academic Press, Chapter 6 by D. C. Roberts and F. Vellaccio.

By "any fibrinogen recognition exosite portion of a hirudin molecule or analogue thereof" is meant any portion of a hirudin molecule or analogue thereof which binds to the fibrinogen recognition exosite of thrombin.

The term <<amino acid residue>> refers to a dehydrated amino acid, for example the glycine residue is:

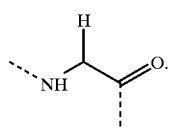

The term <<imino acid residue>> refers to a dehydrated cyclic amino acid, for example the proline is:

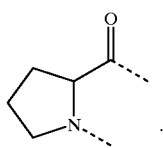

DETAILED DESCRIPTION OF THE INVENTION

Figure 1A:
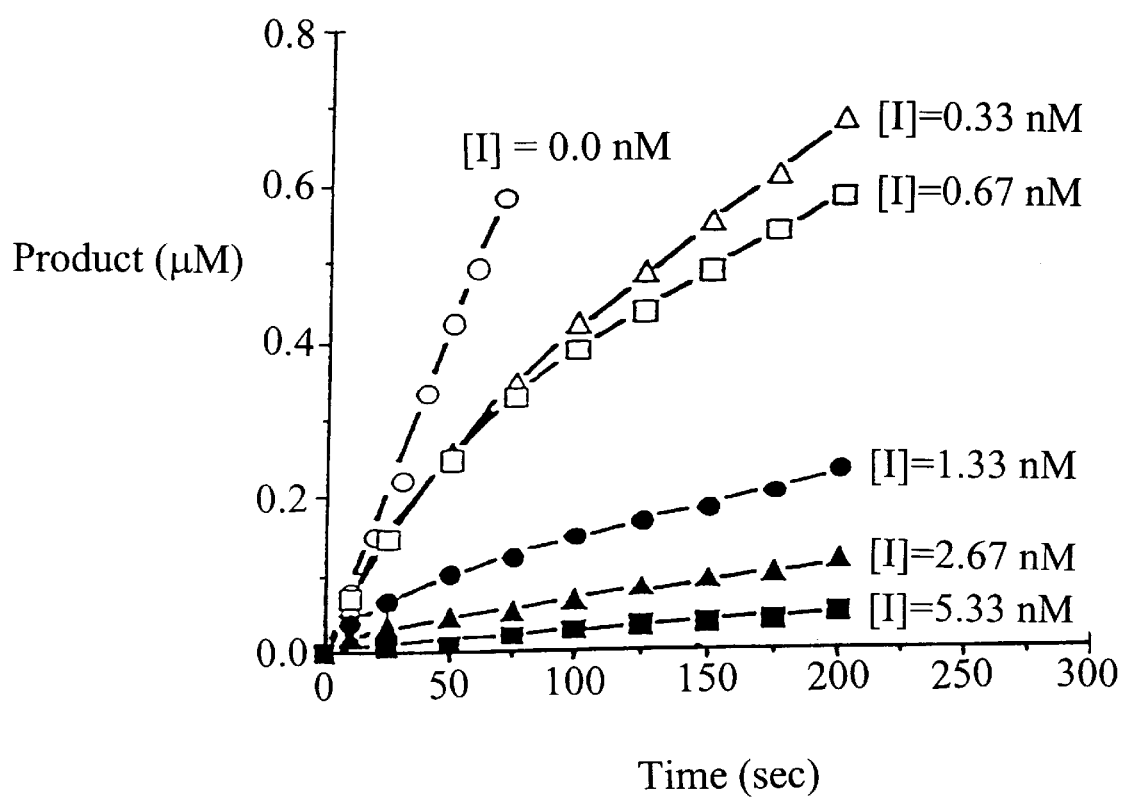

In a preferred embodiment, compounds of this invention are defined by formula (I) wherein, R is selected from the group consisting of:

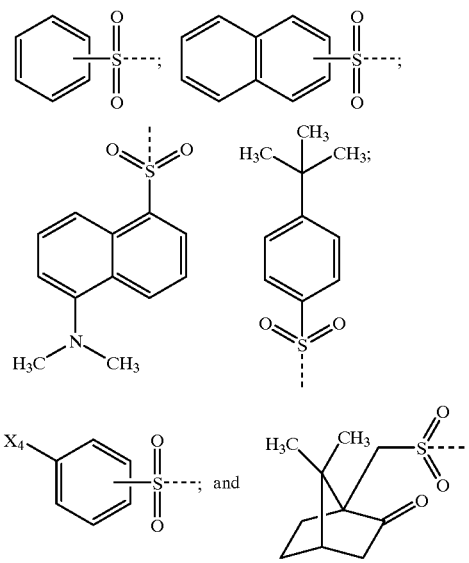

wherein $X_4$ is an halogen (e.g., Cl, Br, or F).

Y is a linear $C_{1-6}$ alkyl, phenyl ethyl or phenylmethyl.

E is guanidyl or hydrogen.

A is selected from the group consisting of tetrahydro isoquinoline carboxylate; L or D-pipecolate; aminocyclohexyl carboxylate; and β-cyclohexyl alanine.

In an alternative preferred embodiment, R is selected from the group consisting of

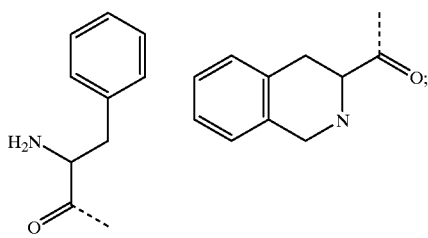

-continued

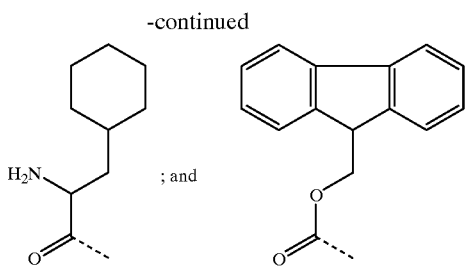

In a preferred embodiment, the chiral center shown as * in formula (I) is in the L configuration.

Preferred compounds if this invention are defined by formula (I) wherein P is defined by formula (X):

G—X$_2$—G$_1$—Q—X$_3$—R$_2$ (SEQ. ID NO: 1)   (X)

wherein,
G and G$_1$ are independently acidic α-amino acid residues;
X$_2$ is any hydrophobic α-amino acid residue;
Q, if present, is a residue derived from an L-α-amino acid or a cyclic imino acid;
X$_3$, if present, is any hydrophobic α-amino acid residue;
R$_2$ is a hydrophobic oligopeptide having all or a portion of the sequence Pro-Glu-Glu-V-W-X, (SEQ. ID NO:2) where V and W are independently hydrophobic amino acid residues and X is selected from the group consisting of D-Glu or L-Glu and Gln; and

wherein each R$_5$ is independently selected from the group consisting of hydrogen, alkyl, aryl, and aralkyl;
with the proviso that P consists of at least 6 amino or imino acid residues.

Z may preferably comprise an alkyl chain wherein said alkyl chain may be interrupted by one or more atoms of O, S, or N atom, carbonyl or amide group.

Z preferably consist of at least 15 atoms in lenght comprising at least one ω-amino acid.

Z preferably consist of at least 15 atoms in lenght comprising at least one α-amino acid.

In a further embodiment Z preferably consist of at least 15 atoms in lenght comprising a combination of at least one ω-amino acid and at least one α-amino acid.

In an alternative preferred embodiment, Z is [NH—(CHR$_6$)$_{1-11}$—CO]$_{1-4}$, [NH—(CH$_2$)$_{1-11}$—CO]$_{1-4}$ or (NHCH$_2$CH=CHCH$_2$CO)$_3$
wherein R$_6$ is an alkyl or any naturally occuring amino acid side chain.

Most preferably, Z is selected from the group consisting of: (12-aminododecanoic acid)-4-aminobutyric acid)-; (12-aminododecanoic acid)-6-aminocaproic acid); (8-aminocapylic acid)-4-aminobutyric acid)-; (11-aminoundecanoic acid)-glycyl); (Glycyl)-12-aminododecanoic acid); (12-aminododecanoic acid)-glycyl); and (β-Alanyl-glycyl-glycyl-5-aminovaleric acid (SEQ. ID NO:3).

X$_2$ is preferably Phe or Tyr.

In a preferred embodiment, G and G$_1$ may independently be:

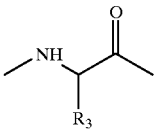

wherein R$_3$ is selected from the group consisting of

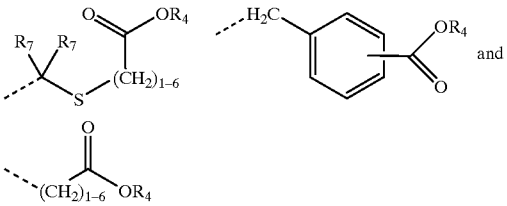

wherein R$_4$ is hydrogen or alkyl; and each R$_7$ is independently CH$_3$ or hydrogen.

In a further preferred embodiment, G and G$_1$ may independently be an aspartic acid residue, a glutamic acid residue or a glutamic alkyl ester residue.

In a most preferred embodiment, G and G$_1$ may independently be aspartic or glutamic acid.

Q is preferably selected from the group consisting of proline residue and glutamic acid residue.

X$_3$ is preferably Ile, Leu, allo-Ile or tert-butyl alanine.

R$_2$ is a hydrophobic oligopeptide having all or a portion of the sequence Pro-Glu-Glu-V-W-X, (SEQ ID NO:4)where V-W is selected from the group consisting of residue of Tyr-Leu, Tyr-Ala, Tyr-(β-Cyclohexylalanine), (β-cyclohexylalanine)-Leu, Pro-Tyr, Ala-(β-cyclohexylalanine), Phe-Tyr and, (β-cyclohexylalanine)-Ala; and X is selected from the group consisting of D-Glu and Gln.

In a preferred embodiment, V-W would be selected from the group consisting of Tyr-Leu, Tyr-Ala, Tyr-Cha, Cha-Leu, and Cha-Ala.

In a further preferred embodiment, the compounds of this invention may be described by formula (II) said formula (II) comprising an active site portion (AS) and a fibrinogen recognition exosite portion (P) linked through a linker (Z):

AS—Z—P   (II)

wherein the (AS) portion is preferably selected from the group consisting of Bzs-Arg-(D-Pip); dansyl-Arg-(D-Pip); dansyl-Arg-(L-Pip); dansyl-Nle-(D-Pip); (D-Phe)-Arg-(D-Pip); Fmoc-Arg-(D-Pip); dansyl-Arg-(D-Tic); dansyl-(D-Arg)-(D-Pip); dansyl-Phe-(D-Pip); dansyl-Cha-(D-Pip); (D-Cha)-Arg-(D-Pip); α-naphthyl sulfonyl-Arg-(D-Pip); β-naphthyl sulfonyl-Arg-(D-Pip); 4-tert-Butyl-benzene sulfonyl-Arg-(D-Pip); dansyl-Arg-(D-Cha); dansyl-Arg-Acha; phenyl ethyl sulfonyl-Arg-(D-Pip); β-dihydroanthracenyl-β-sulfonyl-Arg-(D-Pip); (+)-camphorsulfonyl-Arg-(D-Pip); (D-Tic)-Arg-(D-Pip); 4-bromobenzenesulfonyl-Arg-(D-Pip) and 2,4,6 triisopropylbenzenesulfonyl-Arg-(D-Pip).

The (Z) portion is preferably selected from the group consisting of (12-aminododecanoic acid)-4-aminobutyric acid)-; (12-aminododecanoic acid)-6-aminocaproic acid); (8-aminocapylic acid)-4-aminobutyric acid)-; (12-aminododecanoic acid) -asparagyl-glycyl); (4-aminobutyric acid-glycyl); (5-amino valeric acid)-glycyl); (6-aminocaproic acid)-glycyl); (7-aminoheptanoic acid)-glycyl); (8-aminocapylic acid)-glycyl); (12- aminododecanoic acid); (11-aminoundecanoic acid)-glycyl); (Glycyl)-12-aminododecanoic acid); (12-aminododecanoic acid)-glycyl); and (β-Alanyl-glycyl-glycyl-5-aminovaleric acid) (SEQ ID NO:3).

The (P) portion is preferably selected from the group consisting of Asp-Phe-Glu-Glu-Ile-Pro-Glu-Glu-Tyr-Leu-Gln-OH (SEQ ID NO:5); Asp-Tyr-Glu-Pro-Ile-Pro-Glu-Glu-Ala-(L-β-cyclohexylalanine)-(D-Glu)-OH (SEQ ID NO:6); and Asp-Phe-Glu-Pro-Ile-Pro-Tyr-OH (SEQ ID NO:7).

The biological activity of most of the compounds of this invention were evaluated by two different biological assays. The first assay is an in vitro assay that evaluates the equilibrium dissociation constant ($K_i$) and the inhibitor concentration required to double the time to fibrinogen clot formation ($IC_{50}$). The second assay in an in vivo assay that determines both, the dose of the compounds of this invention necessary to double the occlusion time and the dose of the compounds of this invention necessary to achieve patency at 60 min. in a carotid injury-induced thrombosis.

As FIG. (2b) demonstrates, the compounds of this invention, more specifically, P448 was exposed to three types of proteases: 1) thrombin, which forms a complex with the inhibitor and may hydrolyse it, 2) plasma proteases encountered by inhibitors during the blood circulation, and 3) kidney proteases, which are heavily involved in the clearance of the peptides. The compounds of this invention were very stable to enzyme degradation. The compounds of the present invention show an inhibitory activity comparable to the inhibitory activity of hirudin. For example, table II demonstrate that P448, P531, P532 and P540 have $K_i$ values under 0.032 nM. Table III demontrates that P527, P501, P500 and P513 have $K_i$ values under 0.027 nM. Table IV shows that P535 and P551 have $K_i$ values under 0.00330 nM. Table V shows that BCH-2733 has a $K_i$ of 0.8 nM.

Finally table VI demonstrate the activity of the compounds of this invention in a carotid induced thrombosis model in the rat mediated by $FeCl_3$. For a matter of comparison, two known thrombin inhibitors; Hirulog-8™ and Heparin were also tested. Hirulog-8™ is a thrombin inhibitor having a peptide sequence similar to the peptide sequence of hirudin. The results indicate that the compounds of this invention are capable of inhibiting occlusion in the rat carotid artery at doses in the order of ≧0.25 mg/kg i.v. The more preferred compounds of this invention confer full arterial patency at dose as low as 0.5–1 mg/kg i.v whereas Hirulog-8™ which demonstrates patency at 4 mg/kg..

The preferred compounds of this invention are:
dansyl-Arg-(D-pipecolic acid)-(12-aminododecanoic acid)-4-aminobutyric acid)-Asp-Phe-Glu-Glu-Ile-Pro-Glu-Glu-Tyr-Leu-Gln-OH (P448)(SEQ ID NO:8);
dansyl-Arg-(L-pipecolic acid)-(12-aminododecanoic acid)-4-aminobutyric acid)-Asp-Phe-Glu-Glu-Ile-Pro-Glu-Glu-Tyr-Leu-Gln-OH (P447)(SEQ ID NO:9);
dansyl-Nle-(D-Pipecolic acid)-(12-aminododecanoic acid)-4-aminobutyric acid)-Asp-Phe-Glu-Glu-Ile-Pro-Glu-Glu-Tyr-Leu-Gln-OH (P493)(SEQ ID NO:10);
dansyl-Arg-1,2,3,4-tetrahydroisoquinoline-3-carboxylic acid-(12-aminododecanoic acid)-4-aminobutyric acid)-Asp-Phe-Glu-Glu-Ile-Pro-Glu-Glu-Tyr-Leu-Gln-OH (P471)(SEQ ID NO:11);
dansyl-Arg-(D-β-cyclohexylalanine)-(12-aminododecanoic acid)-4-aminobutyric acid)-Asp-Phe-Glu-Glu-Ile-Pro-Glu-Glu-Tyr-Leu-Gln-OH (P472)(SEQ ID NO:12);
dansyl-Arg-(D)1-amino cyclohexane carboxylic acid-(12-aminododecanoic acid)-4-aminobutyric acid)-Asp-Phe-Glu-Glu-Ile-Pro-Glu-Glu-Tyr-Leu-Gln-OH (P473)(SEQ ID NO:13);
dansyl-(D-Arg)-(D-Pipecolic acid)-(12-aminododecanoic acid)-4-aminobutyric acid)-Asp-Phe-Glu-Glu-Ile-Pro-Glu-Glu-Tyr-Leu-Gln-OH (P492)(SEQ ID NO:14);
dansyl-Phe-(D-Pipecolic acid)-(12-aminododecanoic acid)-4-aminobutyric acid)-Asp-Phe-Glu-Glu-Ile-Pro-Glu-Glu-Tyr-Leu-Gln-OH (P476) (SEQ ID NO:15)
dansyl-Cha-(D-Pipecolic acid)-(12-aminododecanoic acid)-4-aminobutyric acid)-Asp-Phe-Glu-Glu-Ile-Pro-Glu-Glu-Tyr-Leu-Gln-OH (P477)(SEQ ID NO:16);
α-naphthyl sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P531)(SEQ ID NO:17);
β-naphthyl sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P532)(SEQ ID NO:18);
benzyl sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P556)(SEQ ID NO:19);
4-tert-Butyl-benzene sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P552)(SEQ ID NO:20);
(+) 10-camphorsulfonyl-Arg-(D-Pipecolic acid)-(12-aminododecanoic acid)-6-aminocaproic acid-Asp-Phe-Glu-Glu-Ile-Pro-Glu-Glu-Tyr-Leu-Gln-OH (P534)(SEQ ID NO:21);
4-tert-Butyl-benzene sulfonyl-Arg-(D-Pipecolic acid)-(12-aminododecanoic acid)-6-aminocaproic acid-Asp-Phe-Glu-Glu-Ile-Pro-Glu-Glu-Tyr-Leu-Gln-OH (P540)(SEQ ID NO:22);
(D-β-cyclohexylalanine)-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P481) (SEQ ID NO:23);
(D)-1,2,3,4-tetrahydroisoquinoline-3-carboxylic acid-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P482)(SEQ ID NO:24);
(D-Phe)-Arg-(D-Pipecolic acid)(12-aminododecanoic acid)-4-aminobutyric acid)-Asp-Phe-Glu-Glu-Ile-Pro-Glu-Glu-Tyr-Leu-Gln-OH (P483)(SEQ ID NO:25);
fmoc-Arg-(D-Pipecolic acid)(12-aminododecanoic acid)-4-aminobutyric acid)-Asp-Phe-Glu-Glu-Ile-Pro-Glu-Glu-Tyr-Leu-Gln-OH (P484)(SEQ ID NO:26);
dansyl-Arg-(D-Pipecolic acid)-(4-aminobutyric acid)-glycyl)-Asp-Phe-Glu-Glu-Ile-Pro-Glu-Glu-Tyr-Leu-Gln-OH (P514)(SEQ ID NO:27);
dansyl-Arg-(D-Pipecolic acid)-(5-amino valeric acid)-glycyl)-Asp-Phe-Glu-Glu-Ile-Pro-Glu-Glu-Tyr-Leu-Gln-OH (P526)(SEQ ID NO:28);
dansyl-Arg-(D-Pipecolic acid)-(6-aminocaproic acid)-glycyl)-Asp-Phe-Glu-Glu-Ile-Pro-Glu-Glu-Tyr-Leu-Gln-OH (P525)(SEQ ID NO:29);
dansyl-Arg-(D-Pipecolic acid)-(7-aminoheptanoic acid)-glycyl)-Asp-Phe-Glu-Glu-Ile-Pro-Glu-Glu-Tyr-Leu-Gln-OH (P524)(SEQ ID NO:30);
dansyl-Arg-(D-Pipecolic acid)-(8-aminocapylic acid)-glycyl)-Asp-Phe-Glu-Glu-Ile-Pro-Glu-Glu-Tyr-Leu-Gln-OH (P523) (SEQ ID NO:31);
dansyl-Arg-(D-Pipecolic acid)-(12-aminododecanoic acid)-Asp-Phe-Glu-Glu-Ile-Pro-Glu-Glu-Tyr-Leu-Gln-OH (P499)(SEQ ID NO: 32);
dansyl-Arg-(D-Pipecolic acid)-(8-aminocaproicacid)-4-aminobutyric acid)-Asp-Phe-Glu-Glu-Ile-Pro-Glu-Glu-Tyr-Leu-Gln-OH (P528)(SEQ ID NO: 33);

dansyl-Arg-(D-Pipecolic acid)-(11-aminoundecanoic acid)-glycyl)-Asp-Phe-Glu-Glu-Ile-Pro-Glu-Glu-Tyr-Leu-Gln-OH (P527)(SEQ ID NO:34);

dansyl-Arg-(D-Pipecolic acid)-(Glycyl)-12-aminododecanoic acid)-Asp-Phe-Glu-Glu-Ile-Pro-Glu-Glu-Tyr-Leu-Gln-OH (P501)(SEQ ID NO: 35);

dansyl-Arg-(D-Pipecolic acid)-(12-aminododecanoic acid)-glycyl)-Asp-Phe-Glu-Glu-Ile-Pro-Glu-Glu-Tyr-Leu-Gln-OH)(P500)(SEQ ID NO: 36);

dansyl-Arg-(D-Pipecolic acid)-(β-Alanyl-glycyl-glycyl-5-aminovaleric acid)-Asp-Phe-Glu-Glu-Ile-Pro-Glu-Glu-Tyr-Leu-Gln-OH (P498)(SEQ ID NO:37);

dansyl-Arg-(D-Pipecolic acid)-(6-aminocaproic acid-12-aminododecanoic acid)-Asp-Phe-Glu-Glu-Ile-Pro-Glu-Glu-Tyr-Leu-Gln-OH (P513)(SEQ ID NO:38);

dansyl-Arg-(L-Pip)-(4-aminobutyric acid-glycyl)-Asp-Phe-Glu-Glu-Ile-Pro-Glu-Glu-Tyr-Leu-Gln-OH (P409)(SEQ ID NO:39);

dansyl-Arg-(L-Pip)-(5-Aminovaleric acid)-glycyl)-Asp-Phe-Glu-Glu-Ile-Pro-Glu-Glu-Tyr-Leu-Gln-OH (P547) (SEQ ID NO:40);

dansyl-Arg-(L-Pip)-(6-aminocaproic acid)-glycyl)-Asp-Phe-Glu-Glu-Ile-Pro-Glu-Glu-Tyr-Leu-Gln-OH (P408) (SEQ ID NO:41);

dansyl-Arg-(L-Pip)-(7-aminoheptanoic acid)-glycyl)-Asp-Phe-Glu-Glu-Ile-Pro-Glu-Glu-Tyr-Leu-Gln-OH (P548) (SEQ ID NO; 42);

dansyl-Arg-(L-Pip)-(12-aminododecanoic acid)-Asp-Phe-Glu-Glu-Ile-Pro-Glu-Glu-Tyr-Leu-Gln-OH (P550)(SEQ ID NO:43);

dansyl-Arg-(L-pipecolic acid)-(12-aminododecanoic acid)-4-aminobutyric acid)-Asp-Phe-Glu-Glu-Ile-Pro-Glu-Glu-Tyr-Leu-Gln-OH (P447)(SEQ ID NO:44);

dansyl-Arg-(D-pipecolic acid)-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P535)(SEQ ID NO:45);

β-naphthyl sulfonyl-arginyl D-pipecolic acid-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P551) (SEQ ID NO:46);

-4-tert-butylbenzenesulfonyl-Arg-(D-pipecolic acid)-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P553)(SEQ ID NO:47);

α-naphthyl sulfonyl-arginyl D-pipecolic acid-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P581) (SEQ ID NO:48);

tert-butylbezenesulfonyl-Arg (D-Pipecolic acid)-(12-aminododecanoic acid)-4-aminobutyric acid)-Asp-Phe-Glu-Pro-Ile-Pro-Tyr-OH (BCH-2443)(SEQ ID NO:49);

tert-butylbezenesulfonyl-Arg (D-Pipecolic acid)-(12-aminododecanoic acid)-4-aminobutyric acid)-Asp-Phe-Glu-Pro-Ile-Pro-Tyr-OH (BCH-2736)(SEQ ID NO:50);

tert-butylbezenesulfonyl-Arg (D-Pipecolic acid)-(12-aminododecanoic acid)-4-aminobutyric acid)-Asp-Phe-Glu-Pro-Ile-Pro-Tyr-OH (BCH-2741)(SEQ ID NO:51);

4-bromobenzenesulfonyl-Arg (D-Pipecolic acid)-(12-aminododecanoic acid)-4-aminobutyric acid)- Asp-Phe-Glu-Pro-Ile-Pro-Tyr-OH (BCH-2733)(SEQ ID NO: 52); and 2,4,6 triisopropylbenzensulfonyl-Arg (D-Pipecolic acid)-(12-aminododecanoic acid)-4-aminobutyric acid)-Asp-Phe-Glu-Pro-Ile-Pro-Tyr-OH (BCH-2444)(SEQ ID NO:53).

The more preferred compounds of this invention having a $K_i$ value smaller then 1 nM are; (P448); (P471);(P531); (P532); (P552); (P556);(P540); (P534); (P528); (P527); (P500); (P501);(P498); (P513); (P535); (P551); (P581); (P553); and (BCH-2733).

The most preferred compounds of this invention having a $K_i$ value smaller then 0.1 nM are : (P448);(P531);(P532); (P540); (P552); (P527); (P500); (P501); (P513); (P535); (P551); (P553); and (P581).

It should be noted that a person skilled in the art could substitute suitable linkers and synthesize variants of such active bivalent hirudin-like inhibitors. Several such alternative linker segments were synthesized and were found to be effective. Table II discloses several particularly effective examples. In addition to the species discussed supra some other preferred linkers are Ava-glycine, glycine-Ada, Ada-glycine, Bal-glycine-glycine-Ava (SEQ ID NO:54). It should be noted that the bivalent inhibitor sequences exemplified in Table III all use the natural hirudin exosite.

While it may be possible that, for use in therapy, a compound of the invention may be administered as the raw chemical, it is preferable to present the active ingredient as a pharmaceutical formulation.

It will be appreciated by those skilled in the art that the compounds of formula (I) contain at least one chiral centre (shown as * in formula I) and thus exist in the form of two enantiomers and mixtures thereof. All such enantiomers and mixtures thereof are included within the scope of the invention.

It will be appreciated by those skilled in the art that the compounds of formula (I) or (II) may be modified to provide pharmaceutically acceptable salts thereof which are included within the scope of the invention.

Pharmaceutically acceptable salts of the compounds of formula (I) or (II) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

The invention thus further provides a pharmaceutical formulation comprising a compound of formula (I) and (II) and pharmaceutically acceptable acid addition salt thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

In a further embodiment of the present invention is provided the use of a compounds of formula (I) and (II) or a pharmaceutically acceptable salt in the manufacture of a medicament for the treatment of vascular disease in a mammal including human.

In an alternative aspect of the present invention is provided a method for the treatment of vascular disease for the treatment of a mammal, including human comprising the administration of an effective amount of a compound of formula (I) or (II).

It will be appreciated by people skilled in the art that treatment extends to prophylaxis as well to the treatment of established vascular disease.

The compounds of the present invention are useful in combinations, formulations and methods for the treatment and prophylaxis of vascular diseases. These diseases include myocardial infarction, stroke, pulmonary embolism, deep vein thrombosis, peripheral arterial occlusion, restenosis following arterial injury or invasive cardiological procedures, acute or chronic atherosclerosis, edema and inflammation, cancer and metastasis.

The term "combination" as used herein, includes a single dosage form containing at least one compound of this invention and at least one thrombolytic agent, a multiple dosage form, wherein the thrombin inhibitor and the thrombolytic agent are administered separately, but concurrently, or a multiple dosage form wherein the two components are administered separately, but sequentially. In sequential administration, the thrombin inhibitor may be given to the patient during the time period ranging from about 5 hours prior to about 5 hours after administration of the thrombolytic agent. Preferably, the thrombin inhibitor is administered to the patient during the period ranging from 2 hours prior to 2 hours following administration of the thrombolytic agent.

In these combinations, the thrombin inhibitor and the thrombolytic agent work in a complementary fashion to dissolve blood clots, resulting in decreased reperfusion times and increased reocclusion times in patients treated with them. Specifically, the thrombolytic agent dissolves the clot, while the thrombin inhibitor prevents newly exposed, clot-entrapped or clot-bound thrombin from regenerating the clot. The use of the thrombin inhibitor in the formulations of this invention advantageously allows the administration of a thrombolytic reagent in dosages previously considered too low to result in thrombolytic effects if given alone. This avoids some of the undesirable side effects associated with the use of thrombolytic agents, such as bleeding complications.

Thrombolytic agents which may be employed in the combinations of the present invention are those known in the art. Such agents include, but are not limited to, tissue plasminogen activator purified from natural sources, recombinant tissue plasminogen activator, streptokinase, urokinase, purokinase, anisolated streptokinase plasminogen activator complex (ASPAC), animal salivary gland plasminogen activators and known, biologically active derivatives of any of the above.

Various dosage forms may be employed to administer the formulations and combinations of this invention. These include, but are not limited to, parenteral administration, oral administration and topical application. The formulations and combinations of this invention may be administered to the patient in any pharmaceutically acceptable dosage form, including those which may be administered to a patient intravenously as bolus or by continued infusion, intramuscularly—including paravertebrally and periarticularly—subcutaneously, intracutaneously, intra-articularly, intrasynovially, intrathecally, intra-lesionally, periostally or by oral, nasal, or topical routes. Such compositions and combinations are preferably adapted for topical, nasal, oral and parenteral administration, but, most preferably, are formulated for parenteral administration.

Parenteral compositions are most preferably administered intravenously either in a bolus form or as a constant infusion. For parenteral administration, fluid unit dose forms are prepared which contain the compounds of the present invention and a sterile vehicle. The compounds of this invention may be either suspended or dissolved, depending on the nature of the vehicle and the nature of the particular compounds of this invention. Parenteral compositions are normally prepared by dissolving the compounds of this invention in a vehicle, optionally together with other components, and filter sterilizing before filling into a suitable vial or ampule and sealing. Preferably, adjuvants such as a local anesthetic, preservatives and buffering agents are also dissolved in the vehicle. The composition may then be frozen and lyophilized to enhance stability.

Parenteral suspensions are prepared in substantially the same manner, except that the active component is suspended rather than dissolved in the vehicle. Sterilization of the compositions is preferably achieved by exposure to ethylene oxide before suspension in the sterile vehicle. Advantageously, a surfactant or wetting agent is included in the composition to facilitate uniform distribution of its components.

Tablets and capsules for oral administration may contain conventional excipients, such as binding agents, fillers, diluents, tableting agents, lubricants, disintegrants, and wetting agents. The tablet may be coated according to methods well known in the art. Suitable fillers which may be employed include cellulose, mannitol, lactose and other similar agents. Suitable disintegrants include, but are not limited to, starch, polyvinylpyrrolidone and starch derivatives, such as sodium starch glycolate. Suitable lubricants include, for example, magnesium stearate. Suitable wetting agents include sodium lauryl sulfate.

Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives. These include suspending agents, such as sorbitol, syrup, methyl cellulose, gelatin, hydroxyethylcellulose, carboxymethylcellulose, aluminum stearate gel or hydrogenated edible fats, emulsifying agents which include lecithin, sorbitan monooleate, polyethylene glycols, or acacia, non-aqueous vehicles, such as almond oil, fractionated coconut oil, and oily esters, and preservatives, such as methyl or propyl p-hydroxybenzoate or sorbic acid.

Formulations for topical administration may, for example, be in aqueous jelly, oily suspension or emulsified ointment form.

The dosage and dose rate of the compounds of this invention will depend on a variety of factors, such as the weight of the patient, the specific pharmaceutical composition used, the object of the treatment, i.e., therapy or prophylaxis, the nature of the thrombotic disease to be treated, and the judgment of the treating physician.

According to the present invention, a preferred pharmaceutically effective daily dose of the compounds of this invention is between about 1 µg/kg body weight of the patient to be treated ("body weight") and about 5 mg/kg body weight. In combinations containing a thrombolytic agent, a pharmaceutically effective daily dose of the thrombolytic is between about 10% and 80% of the conventional dosage range. The "conventional dosage range" of a thrombolytic agent is the daily dosage used when that agent is employed in a monotherapy [physician's Desk Reference 1989, 43rd Edition, Edward R. Barnhart, publisher]. That conventional dosage range will, of course, vary depending on the thrombolytic agent employed. Examples of conventional dosage ranges are as follows: urokinase—500,000 to 6,250,000 units/patient, streptokinase—140,000 to 2,500,000 units/patient, tPA—0.5 to 5.0 mg/kg body weight, ASPAC—0.1 to 10 units/kg body weight.

Most preferably, the therapeutic and prophylactic compositions of the present invention comprise a dosage of between about 10 µg/kg body weight and about 500 µg/kg body weight of the compounds of this invention. Most preferred combinations comprise the same amount of the compounds of this invention and between about 10% and about 70% of the conventional dosage range of a thrombolytic agent. It should also be understood that a daily pharmaceutically effective dose of either the compounds of this invention or the thrombolytic agent present in combinations of the invention, may be less than or greater than the specific ranges cited above.

Once improvement in the patient's condition has occurred, a maintenance dose of a combination or composition of this invention is administered, if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment upon any recurrence of disease symptoms.

According to an alternate embodiment of this invention, compounds may be used in compositions and methods for coating the surfaces of invasive devices, resulting in a lower risk of clot formation or platelet activation in patients receiving such devices. Surfaces that may be coated with the compositions of this invention include, for example, prostheses, artificial valves, vascular grafts, stents and catheters. Methods and compositions for coating these devices are known to those of skill in the art. These include chemical cross-linking or physical adsorption of the compounds of this invention-containing compositions to the surfaces of the devices. According to a further embodiment of the present invention, compounds may be used for ex vivo thrombus imaging in a patient. In this embodiment, the compounds of this invention are labelled with a radioisotope. The choice of radioisotope is based upon a number of well-known factors, for example, toxicity, biological half-life and detectability. Preferred radioisotopes include, but are not limited to $^{125}$I, $^{123}$I and $^{111}$I. Techniques for labelling the compounds of this invention are well known in the art. Most preferably, the radioisotope is $^{123}$I and the labelling is achieved using $^{123}$I-Bolton-Hunter Reagent. The labelled thrombininhibitor is administered to a patient and allowed to bind to the thrombin contained in a clot. The clot is then observed by utilizing well-known detecting means, such as a camera capable of detecting radioactivity coupled to a computer imaging system. This technique also yields images of platelet-bound thrombin and meizothrombin.

This invention also relates to compositions containing the compounds of this invention and methods for using such compositions in the treatment of tumor metastases. The efficacy of the compounds of this invention for the treatment of tumor metastases is manifested by the inhibition inhibitors to inhibit thrombin-induced endothelial cell activation. This inhibition includes the repression of platelet activation factor (PAF) synthesis by endothelial cells. These compositions and methods have important applications in the treatment of diseases characterized by thrombin-induced inflammation and edema, which is thought to be mediated be PAF. Such diseases include, but are not limited to, adult respiratory distress syndrome, septic shock, septicemia and reperfusion damage. Early stages of septic shock include discrete, acute inflammatory and coagulopathic responses. It has previously been shown that injection of baboons with a lethal dose of live *E. coli* leads to marked declines in neutrophil count, blood pressure and hematocrit. Changes in blood pressure and hematocrit are due in part to the generation of a disseminated intravascular coagulopathy (DIC) and have been shown to parallel consumption of fibrinogen [F. B. Taylor et al., "Protein C Prevents the Coagulopathic and Lethal Effects of *Escherichia coli* infusion in the Baboon", J.Clin.Invest., 79, pp. 918–25 (1987)]. Neutropenia is due to the severe inflammatory response caused by septic shock which results in marked increases in tumor necrosis factor levels. The compounds of this invention may be utilized in compositions and methods for treating or preventing DIC in septicemia and other diseases.

This invention also relates to the use of the above-described compounds, or compositions comprising them, as anticoagulants for extracorporeal blood. As used herein, the term "extracorporeal blood" includes blood removed in line from a patient, subjected to extracorporeal treatment, and then returned to the patient in such processes as dialysis procedures, blood filtration, or blood bypass during surgery. The term also includes blood products which are stored extracorporeally for eventual administration to a patient and blood collected from a patient to be used for various assays. Such products include whole blood, plasma, or any blood fraction in which inhibition of coagulation is desired.

The amount or concentration of compounds of this invention in these types of compositions is based on the volume of blood to be treated or, more preferably, its thrombin content. Preferably, an effective amount of a compounds of this invention of this invention for preventing coagulation in extracorporeal blood is from about 1 $\mu$g/60 ml of extracorporeal blood to about 5 mg/60 ml of extracorporeal blood.

The compounds of this invention may also be used to inhibit clot-bound thrombin, which is believed to contribute to clot accretion. This is particularly important because commonly used anti-thrombin agents, such as heparin and low molecular weight heparin, are ineffective against clot-bound thrombin. Finally, the compounds of this invention may be employed in compositions and methods for treating neurodegenerative diseases. Thrombin is known to cause neurite retraction, a process suggestive of the rounding in shape changes of brain cells and implicated in neurodegenerative diseases, such as Alzheimer's disease and Parkinson's disease. In order that the invention described herein may be more fully understood, the following examples are set forth. It should be understood that these examples are for illustrative purposes only and are not to be construed as limiting this invention in any manner.

EXAMPLES

Example 1

Experimental Procedures

Materials.

Human α-thrombin (3,000 NIH units/mg), bovine fibrinogen (~70% of protein, 85% of protein clottable), Tos-Gly-Pro-Arg-AMC.HCl salt, poly(ethylene glycol) 8000™, Ada and Tris were purchased from Sigma Inc. AMC dansyl chloride, 1-naphthalenesulfonyl chloride, 2-naphthalenesulfonyl chloride, 4-tert-butylbenzenesulfonyl chloride, Ada, Ava and D,L-Pip were were obtained from Aldrich. Boc-Abu, Boc-Bal, Boc-Aca, Boc-Aha, Boc-Cha, Boc-D-Cha, Boc-L-Pip, Boc-D-Pip, and Boc-D-Tic were purchased from BaChem. Acha was obtained from Fluka Inc. Boc-Ada, Boc-D,L-Pip, and Boc-Acha were prepared according to the procedure described by Chaturvedi, D. N., Knittel, J. J., Hruby, V. J., Castrucci, A. M., & Hadley, M. E. (1984) *J. Med. Chem.* 27, 1406–1410 which is hereby incorporated by reference. All other amino acid derivatives for peptide synthesis were purchased from Advanced ChemTech except Boc-Glu(OBzl)-OH, which was obtained from Sigma. The side chain protecting groups for Boc-amino acids were benzyl for glutamic acid (Glu) and aspartic acid (Asp), tosyl (Tos) for arginine (Arg) and 2-bromobenzyloxycarbonyl for tyrosine (Tyr). Boc-Gln-OCH$_2$-phenylacetylamidomethyl resin (0.714 mmol/g) and p-methyl-benzhydrylamin resin (0.770 mmol/g) were purchased from Applied Biosystems Inc. Boc-D-Glu(OBzl()-

OCH2-pheynylacetylamidomethyl resin (0.31 mmol/g) was purchased from Peninsula Laboratories, Inc. The solvents for peptide synthesis were obtained from B&J Chemicals and Applied Biosystems Inc. Citric acid was purchased from Anachemia. HF and TFA were purchased from Matheson and Halocarbon Products Co., respectively.

Peptide Synthesis

The peptides were prepared according to the method described in Szewczuk, Z., Gibbs, B. F., Yue, S.-Y., Purisima, E., & Konishi, Y. (1992) *Biochemistry* 31, 9132–9140 which is hereby incorporated by reference. Final products were obtained as lyophilizates with 98% or higher purity estimated by analytical HPLC. The purified peptides were identified by amino acid analysis on a Beckman Model 6300™ high performance analyzer and by molecular mass analysis using a SCIEX API III™ mass spectrometer. Peptide contents in lyophilizates were determined by the amino acid analysis. Following this procedure, the following peptides were synthesized: P429, P428, P431, P430, P396, P448, P447, P471, P472, P473, P476, P477, P493, P492, P531, P532, P556, P552, P540, P534, P482, P482, P483, P484, P514, P526, P525, P524, P523, P499, P528, P527, P501, P500, P498, P513, P409-2, P547, P408-2, P548, P550, P447, P535, P551, P553, P581, BCH-2443, BCH-2736, BCH-2741, BCH-2733, and BCH-2444.

Example 2

Proteolytic assays

Proteolytic stabilities of the compounds of this invention against human a-thrombin and human plasma proteases were measured as described in Szewczuk et al., 1993, supra, and Szewczuk et al., 1992, supra, respectively. Proteolytic stability of the inhibitors against proteases on kidney membranes was measured as follows: The preparation of kidney membranes was carried out at 0–4° C. according to the procedure (method 3) of Maeda, T., Balakrishnan, K., & Mehdi, S. Q. (1983) *Biochim. Biophys. Acta* 731, 115–120. The kidneys of Sprague-Dawley™ rats were minced finely with surgical scissors. The tissue (1 g) was then added to 3 mL of homogenization buffer (10 mM sodium phosphate buffer, pH 7.4, containing 1 mM MgCl2, 30 mM NaCl, 0.02% NaN3 and 10 μg/L of DNase) and homogenized using a Polytron* homogenizer (Brinkmann). For sufficient cell disruption, the tissue was subject to five or six bursts for 5 seconds each time at a power setting of 7 separated by 1 to 2 minutes of cooling. About 10 mL of the homogenate was layered over 10 mL of a 41% (w/v) solution of sucrose and centrifuged in a Beckman SW27™ swinging bucket rotor (100000× g for 30 minutes). The interfacial membranes were collected and washed twice with 10 mM Tris Hcl buffer, pH 7.4. The suspension of the membranes in the same buffer was stored in small aliquots at −80° C. until they were used. The protein content of the suspension were determined before the storage by amino acid analysis. An aliquot of kidney membrane (3 mg) and 3 nM of the inhibitor were then incubated in 0.6 mL of 10 mM sodium phosphate buffer, pH 7.4, containing 1 mM MgCl2, 30 mM NaCl, 0.02% $NaN_3$ and 10 μg/L of DNase, for digestion at 37° C. An aliquot (0.15 mL) of the reaction solution was sampled at 0, 15 and 30 minutes of the reaction time. The reaction was terminated by heating at 100° C. in a boiling water for 2 minutes. The sample was subsequently spun at 6000× g for 2 minutes and the supernatant was injected onto a Hewlett Packard Model 1090™ HPLC. The inhibitors and their metabolites were isolated on an analytical C18 column (4.6×250 mm, Vydac*) with a linear gradient from 10 to 70% of acetonitrile gradient containing 0.1% trifluoroacetic acid over 60 minutes at a flow rate of 1 mL/min. The elution profile was monitored by the absorbance at 210 nm. The peptides were collected and identified by the amino acid analysis described in Szewczuk et al., 1992, supra.

Figure 1B:
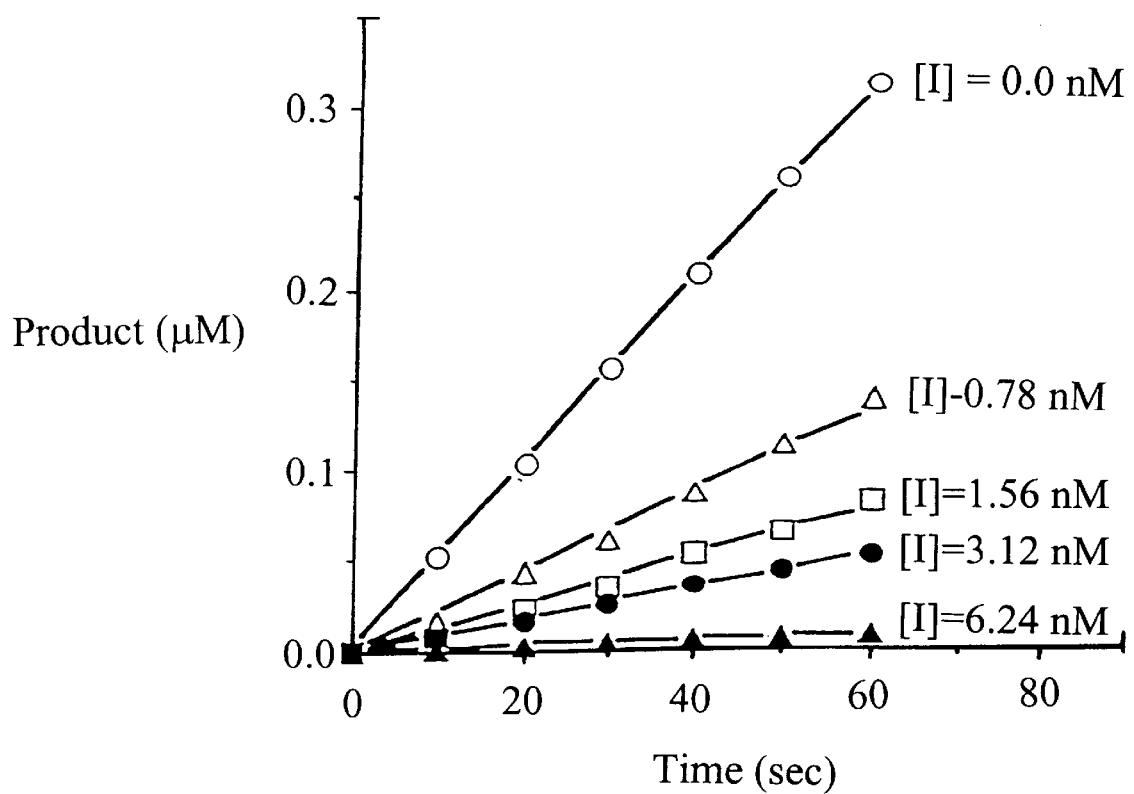
Figure 2A:
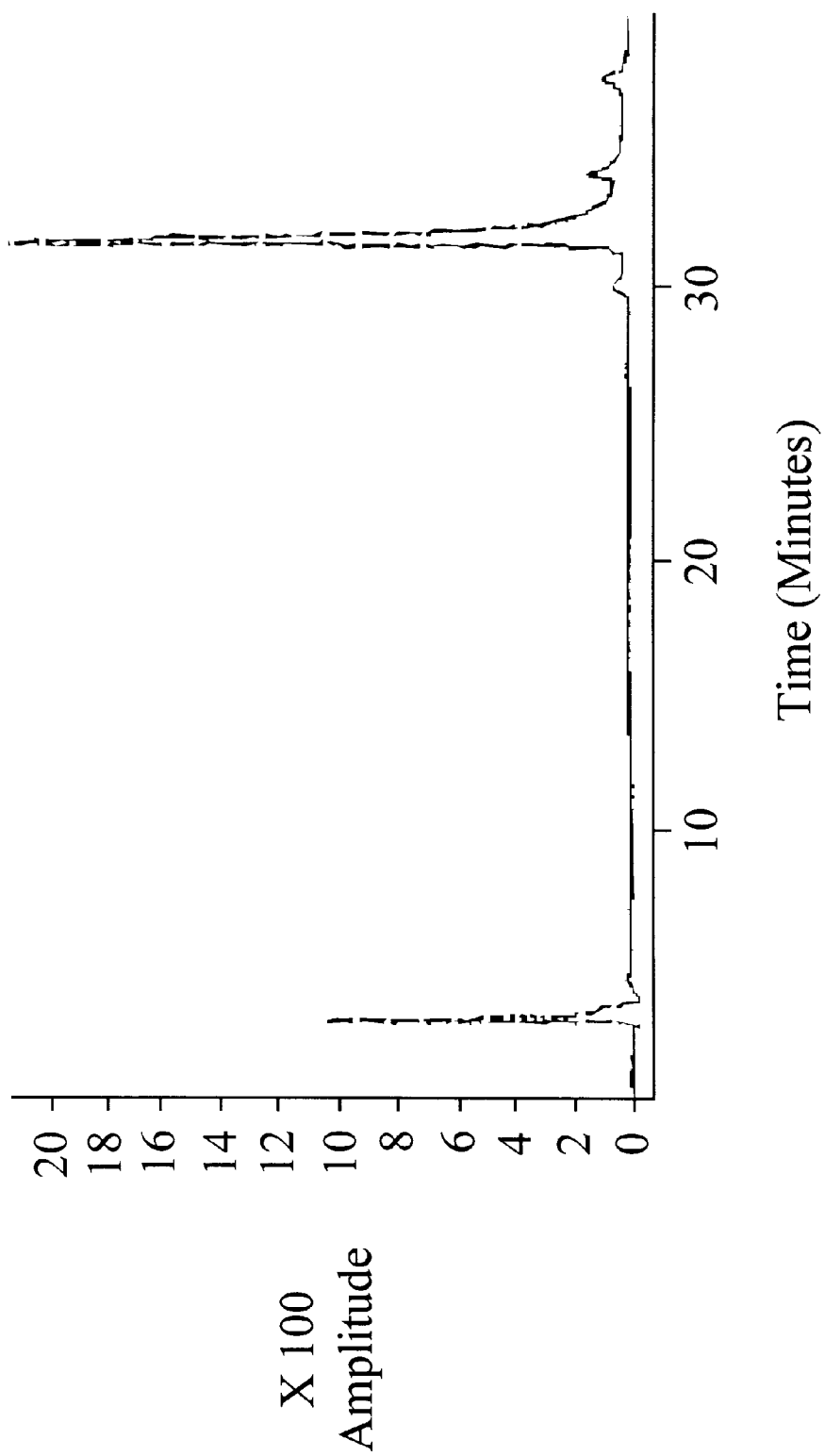
Figure 2B:
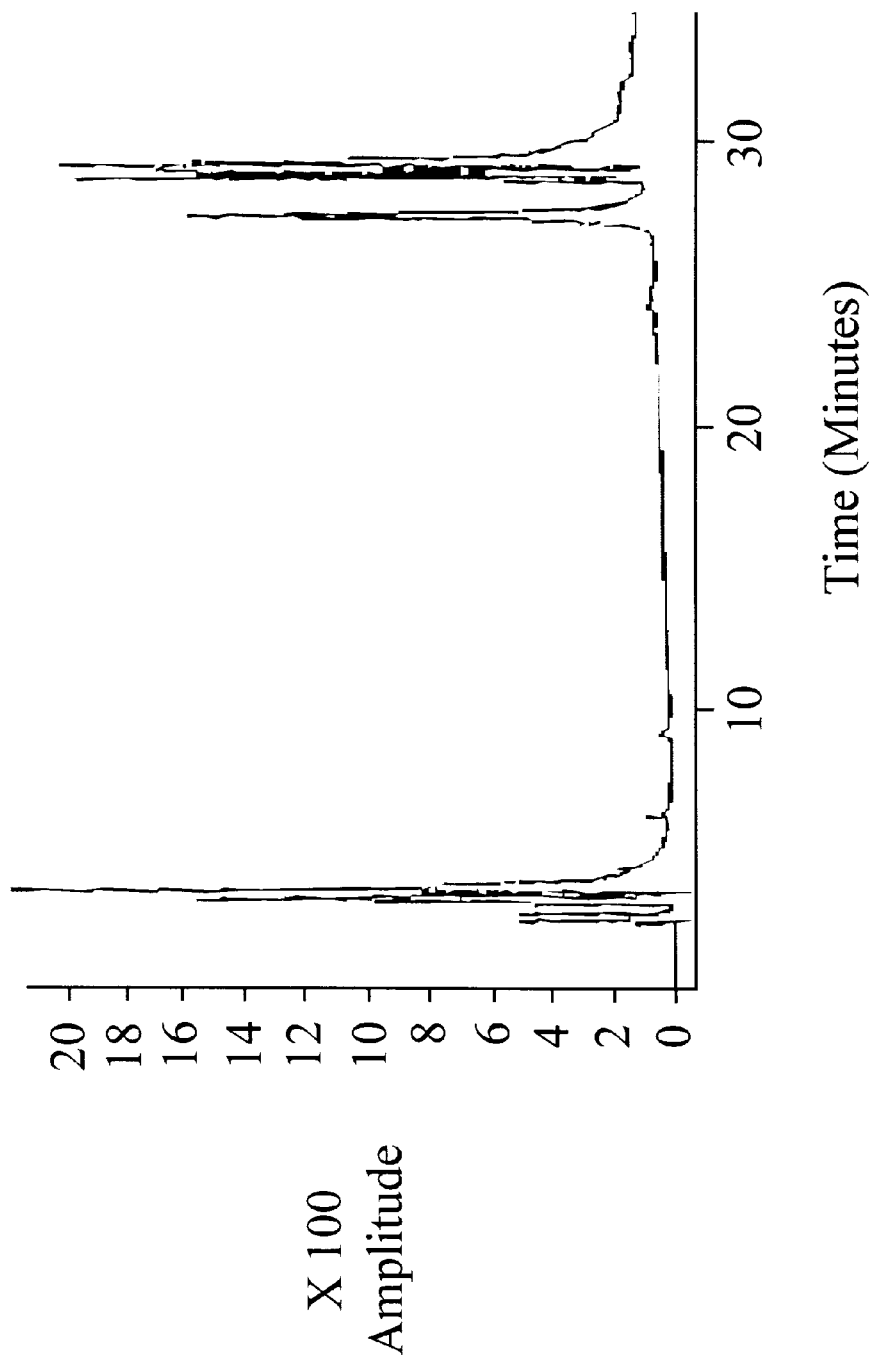

Materials. The chromogenic and fluorogenic substrates Tosyl-Gly-Pro-Arg-pNA and Tos-Gly-Pro-Arg-AMC were purchased from Boehringer Manheim and Sigma, respectively. Fibrinogen and bovine or human α-thrombins were from Sigma and purity was confirmed by sodium inhibitor dissolved in the same buffer. Initial velocities were recorded at several inhibitor concentrations and kinetic parameters were determined by fitting the data to a general equation describing enzyme inhibition (Segel, 1975). The data were analyzed using the non-linear regression program RNLIN in the IMSL library (IMSL, 1987) on a microVAX™ 3500 computer. Dixon and Lineweaver-Burk plots were constructed to qualitatively assign the type of inhibition exhibited by each peptide. Fluorogenic assays were conducted using the same conditions and instrument as above operating in the fluorescence mode in the ratio ($\lambda_{ex}$=383 nm, $\lambda_{em}$=455 nm) Fluorescence intensities were calibrated with 7-amino-4-methyl coumarin solution of known concentration The results are demonstrated in FIGS. 1 and 2.

Example 3

Fibrin Clotting and Amidolytic Assays

Materials. The chromogenic and fluorogenic substrates Tosl-Gly-Pro-Arg-ρNA and Tos-Gly-Pro-Arg-AMC were purchased from Boehringer Manheim and Sigma, respectively. Fibrinogen and bovine or human α-thrombins were from Sigma and purity was confirmed by sodium inhibitor dissolved in the same buffer.

The fibrin clotting assay was performed in 50 mM Tris HCl buffer (pH 7.52 at 37° C.) containing 0.1 M NaCl and 0.1% poly(ethylene glycol) 8000 with 9.0×10-10 M (0.1 NIH unit/mL) and 0.03% (w/v) of the final concentrations of human thrombin and bovine fibrinogen, respectively, as reported elsewhere (Szewczuk et al., 1992). The clotting time was plotted against the inhibitor concentrations and the IC50 was estimated as the inhibitor concentration required to double the clotting time relative to the control.

Determination of Thrombin Inhibitory Dissociation Constants $K_I$

The inhibition of the amidolytic activity of human thrombin was measured fluorometrically using Tos-Gly-Pro-Arg-AMC as a fluorogenic substrate in 50 mM Tris-HCl buffer (pH 7.52 at 37° C.) containing 0.1 M NaCl and 0.1% poly(ethylene glycol) 8000 at room temperature (Szewczuk et al., 1992). The final concentrations of the inhibitors, the substrate and human thrombin were 0.1–5-fold of Ki, 1–8× $10^{-5}$ M and 6.0×$10^{-11}$ M, respectively for the data in Table 1. For data in Tables II and III, the corresponding concentrations were 0.5-™1000-fold of Ki, 1–8×$10^{-6}$ M and 3.0× $10^{-11}$ M, respectively, if K, >$10^{-10}$ M, and 10–100-fold of Ki, 5–40×$10^{-6}$ M and 3.0 $10^{-11}$ M, respectively, if Ki<$10^{-10}$ M. The hydrolysis of the substrate by thrombin was monitored on a Varian-Cary 2000™ spectrophotometer in the fluorescence mode ($\lambda$eX=383 nm, $\lambda$em=455 nm) or on a Hitachi F2000™ fluorescence spectrophotometer ($\lambda_{ex}$=383 nm, $\lambda_{em}$=455 nm), and the fluorescent intensity was calibrated using AMC. The reaction reached a steady-state within 3 min after mixing thrombin with the substrate and an inhibitor. The steady-state velocity was then measured for a few minutes. The compounds of this invention were also pre-incubated with thrombin for 20 min at room temperature before adding the substrate. The steady-state was achieved within 3 min and measured for a few min. The kinetic data (the steady-state velocity at various concentrations of the substrate and the inhibitors) of the competitive inhibition was analyzed using the methods described by Segel (1975). A non-linear regression program, RNLIN in the IMSL library (IMSL, 1987), LMDER in MINPACK library (More et al., 1980) or Microsoft™ Excell™, was used to estimate the kinetic parameters ($K_m$, $V_{max}$ and $K_i$). The biological data are reported on tables I–V.

TABLE I

Activities of the Thrombin Active Site Directed inhibitors

| Peptide | Sequence | $K_i$(nm) | $IC_{50}$(nM) |
|---|---|---|---|
| P429 | Dansyl-Arg-(D-Pipecolic acid)-$NH_2$ | 158 ± 57 | 430 ± 130 |
| P428 | Dansyl-Arg-(L-Pip)-$NH_2$ | 19100 ± 1300 | 37900 ± 1900 |
| P431 | Dansyl-Arg-(D-Pipecolic acid)-Abu-$NH_2$ | 980 ± 130 | 2580 ± 680 |
| P430 | Dansyl-Arg-(L-Pip)-Abu-$NH_2$ | 11600 ± 3300 | 39100 ± 7200 |
| P396 | Dansyl-Arg-(D-Tic)-$NH_2$ | 390 ± 20 | 820 ± 150 |

TABLE II

Activity of Thrombin Inhibitors with Various Active Site Inhibitor Segments

| PEPTIDE | Structure of active site inhibitor segment | $K_i$ (nM) |
|---|---|---|
| P448 (SEQ ID NO:8) | Dansyl-Arg-(D-Pipecolic acid)[a] | 0.0170 ± 0.0042 |
| P447 (SEQ ID NO:9) | Dansyl-Arg-(L-Pip)[a] | 12.4 ± 1.8 |
| P471 (SEQ ID NO:11) | Dansyl-Arg-(D-Tic)[a] | 0.285 ± 0.040 |
| P472 (SEQ ID NO:12) | Dansyl-Arg-(D-(Cha)[a] | 17.1 ± 3.1 |
| P473 (SEQ ID NO:13) | Dansyl-Arg-D-(Acha)[a] | 36.3 ± 10.3 |
| P476 (SEQ ID NO: 15) | Dansyl-Phe-(D-Pipecolic acid)[a] | 2.62 ± 0.20 |
| P477 (SEQ ID NO:16) | Dansyl-cha-(D-Pipecolic acid)[a] | 5.85 ± 0.098 |
| P493 (SEQ ID NO: 10) | Dansyl-Nle-(D-Pipecolic acid)[a] | 5.20 ± 1.31 |
| P492 (SEQ ID NO:14) | Dansyl-(D-Arg)-(D-Pipecolic acid)[a] | 1.02 ± 0.38 |
| P531 (SEQ ID NO:17) | α-Nas-Arg-(D-Pipecolic acid)[a] | 0.032 ± 0.001 |
| P532 (SEQ ID NO:18) | β-Nas-Arg-(D-Pipecolic acid)[a] | 0.024 ± 0.004 |
| P556 (SEQ ID NO:19) | Bzs-Arg-(D-Pipecolic acid)[a] | 0.137 ± 0.026 |
| P552 (SEQ ID NO:20) | tBbs-Arg-(D-Pipecolic acid)[a] | 0.0170 ± .0004 |
| P540 (SEQ ID NO:22) | tBbs-Arg-(D-Pipecolic acid)[b] | 0.0053 ± 0.0006 |
| P534 (SEQ ID NO: 21) | (+) 10-camphorsulfonyl-Arg-(D-Pipecolic acid)[b] | 0.108 ± 0.001 |
| P481 (SEQ ID NO:23) | (D-Cha)-Arg-(D-Pipecolic acid)[a] | 9.51 ± 0.16 |
| P482 (SEQ ID NO: 24) | (D-Tic)-Arg-(D-Pipecolic acid)[a] | 12.2 ± 3.2 |
| P483 (SEQ ID NO:25) | (D-Phe)-Arg-(D-Pipecolic acid)[a] | 54.9 ± 6.6 |
| P484 (SEQ ID NO:26) | fmoc-Arg-(D-Pipecolic acid)[a] | 14.8 ± 1.2 |
| | Hirudin | 0.00028 |

[a]The linker and exosite inhibitor segments comprise the sequence Ada-Abu-DFEEIPEEYLQ-OH.
[b]The linker and exosite inhibitor segments comprise the sequence Ada-Aca- DFEEIPEEYLQ-OH.

TABLE III

Activity of Thrombin Inhibitors with Various Linker Serments

| Peptide | Structure of Linker Segment | Atom No. Lenght | $K_i$ (nM) |
|---|---|---|---|
| P514 (SEQ ID NO:27) | Abu-Gly[a] | 8 | 6800 ± 1640 |
| P526 (SEQ ID NO:28) | Ava-Gly[a] | 9 | 4970 ± 260 |
| P525 (SEQ ID NO:29) | Aca-Gly[a] | 10 | 3000 ± 830 |
| P524 (SEQ ID NO: 30) | Aha-Gly[a] | 11 | 1480 ± 170 |
| P523 (SEQ ID NO:31) | Aca*-Gly[a] | 12 | 148 ± 9 |
| P499 (SEQ ID NO:32) | Ada[a] | 13 | 20.0 ± 4.0 |
| P528 (SEQ ID NO:33) | Aca*-Abu[a] | 14 | 0.521 ± 0.086 |
| P527 (SEQ ID NO:34) | Aua-Gly[a] | 15 | 0.0260 ± 0.0044 |
| P501 (SEQ ID NO: 35) | Gly-Ada[a] | 16 | 0.0271 ± 0.0067 |
| P500 (SEQ ID NO:36) | Ada-Gly[a] | 16 | 0.0255 ± 0.0100 |
| P498 (SEQ ID NO:37) | βAla-Gly-Gly-Ava[a] | 16 | 0.131 ± 0.022 |
| P448 (SEQ ID NO: 8) | Ada-Abu[a] | 18 | 0.0170 ± 0.0042 |
| P513 (SEQ ID NO:38) | Ada-Aca[a] | 20 | 0.0155 ± 0.0026 |
| P409 (SEQ ID NO: 39) | Abu-Gly[b] | 8 | no inhibition |
| P547 (SEQ ID NO: 40) | Ava-Gly[b] | 9 | — |
| P408 (SEQ ID NO: 41) | Aca-Gly[b] | 10 | 124 ± 61 |
| P548 (SEQ ID NO: 42) | Aha-Gly[b] | 11 | — |
| P550 (SEQ ID NO: 43) | Ada[b] | 13 | — |

TABLE III-continued

Activity of Thrombin Inhibitors with Various Linker Serments

| Peptide | Structure of Linker Segment | Atom No. Lenght | Ki (nM) |
|---|---|---|---|
| P447 (SEQ ID NO: 44) | Ada-Abu[b] | 18 | 12.4 ± 1.8 |
| | Hirudin | | 0.00028 |

[a]The active site inhibitor and exosite inhibitor segments comprise the sequences dansyl-Arg-(D-Pipecolic acid) and DFEEIPEEYLQ-OH, respectively.
[b]The active site inhibitor and exosite inhibitor segments conprise the sequences densyl-Arg-(L-Pip) and DFEEIPEEYLQ-OH, respectively.

TABLE IV

Activity of Thrombin Inhibitors with Various Exosite Inhibitor Serments

| Peptide | Structure of active,site inhibitor segment | Structure of,exosite inhibitor segment | $K_i$ (Nm) |
|---|---|---|---|
| P535 (SEQ ID NO:45) | Dansyl-Arg-(D-Pipecolic acid)[a] | DYEPIPEEA-(Cha)-(D-Glu)-OH | 0.00123 ± 0.00026[1] 0.0020 ± 0.0004[2] |
| P551 (SEQ ID NO:46) | β-Nas-Arg-(D-Pipecolic acid)[a] | DYEPIPEEA-(Cha)-(D-Glu)-OH | 0.00330 ± 0.00016[1] 0.0042 ± 0.0002[2] |
| P553 (SEQ ID NO:47) | tBbs-Arg-(D-Pipecolic acid)[a] | DYEPIPEEA-(Cha)-(D-Glu)-OH | 0.0030 ± 0.0004 |
| P581 (SEQ ID NO:48) | α-Nas-Arg-(D-Pipecolic acid)[a] | DYEPIPEEA-(Cha)-(D-Glu)-OH | 0.0145 ± 0.0009 |

[a]the linker segment comprise the sequences (12-aminododecanoic acid) - (4-aminobutyric acid)
[1]results from assay no. 1
[2]results from assay no. 2

TABLE V

Activity of Thrombin Inhibitor

| Peptide | Active site | Linker | Exosite | Ki | $IC_{50}$(dtt) |
|---|---|---|---|---|---|
| BCH-2443 (SEQ ID NO:49) | tBbs-Arg (D-Pipecolic acid) | Ada-Abu | DFEPIPY-OH | 1 nM | 12.0 nM |
| BCH-2736 (SEQ ID NO:50) | tBbs-Arg (D-Pipecolic acid) | Ada-Abu | DFEPIPY-OH | 270 nM | 1.1 μM |
| BCH-2741 (SEQ ID NO: 51) | tBbs-Arg (D-Pipecolic acid) | Ada-Abu | DFEPIPY-OH | not tested due to insolubility | |
| BCH-2733 (SEQ ID NO:52) | BrBs-Arg (D-Pipecolic acid) | Ada-Abu | DFEPIPY-OH | 0.8 nM | 4.1 nM |
| BCH-2444 (SEQ ID NO:53) | tipBs-Arg (D-Pipecolic acid) | Ada-Abu | DFEPIPY-OH | 5.5 nM | 55.0 nM |

Example 4

FeCl₃ Induced Arterial Injury Model
Specie: Rat, male, Sprague-Dawley.
Weight: 375–450 g
Experimental Study The FeCl3 induced arterial injury model assays were conducted according to Kurz, K. D., Main, R. W., Sandusky, G. E., Thrombosis research 60; 269–280, 1990 and Schumacher, W. A. et al. J. pharmacology and experimental therapeutics 267; 1237–1242, 1993.

Male, Sprague-Dawley (375–450 g) are anesthetized with Urethane (1500 mg/kg IP). Animals are laid on a heating pad which is maintained at 37° C. The carotid artery is approached through a midline cervical incision. Carefully blunt dissection is used to expose and isolate the vessel from the carotid sheath. Using forceps, the artery is lifted to provide clearance to insert two small polyethylene tubing (PE-205) underneath it. The temperature probe (Physitemp MT23/3 )™ is placed between the PE-205 and the artery. The vessel temperature is monitored for 60 minutes after application of FeCl₃. Vessel temperature changes are recorded on a thermister (Cole-Palmer Model 08533-41). Injury is induced by application of a small disc (3 mm dia.) of Whatman™ No.1 filter paper previously dipped in a 35% solution of FeCl₃ on the carotid artery above the temperature probe. The site of the experiment is covered with in Aluminum foil in order to protect the FeCl₃ from degradation by light.

The time between the Ferric Chloride application and the time at which the vessel temperature decreases abruptly (>2.4° C.), is recorded as the time to occlusion (TTO) of the vessel.

Before the start of the experiment, one blood sample is drawn (1 ml) in a tube of 0.105M buffered citrate solution (from the eye's sinus) and the animal is exsanguinated at the end. All the samples are kept on ice and centrifuged as soon as possible at 2000 Rpm for 10 min., 4° C. The plasma is analyzed in duplicate for activated partial thromboplastin time on a haemostasis analyzer (STAGO ST4™).

From a group of four animals, two arteries are stored at −80C for further analysis. The others are observed under a light microscope at 40× (Leica™) for quantification of the occlusion (complete, partial, no occlusion). The biological data are reported on table VI.

TABLE VI

Activity of Thrombin Inhibitor in a Carotid injury-induced Thrombosis

| Peptide | Active site | Linker | Exosite | Dose to double occlusion time (mg/kg i.v. bolus)[1] | Dose to achieve patency at 60 min. (mg/kg i.v. bolus)[2] |
|---|---|---|---|---|---|
| P448 (SEQ ID NO:8) | Dansyl-Arg-(D-Pipecolic acid) | Ada-Abu | DFEEIPEEYLQ-OH | 1.0 (N = 3) | not achieved at 2 (N = 3) |
| P531 (SEQ ID NO:17) | αNas-Arg (D-Pipecolic acid) | Ada-Abu | DFEEIPEEYLQ-OH | 0.5 (N = 4) | not achieved at 2 (N = 4) |
| P540 (SEQ ID NO:22) | TBbs-Arg-(D-Pipecolic acid) | Ada-Aca | DFEEIPEEYLQ-OH | 0.5 (N = 4) | Not achieved at 2 (N = 4) |
| P551 (SEQ ID NO:46) | βnas-Arg (D-Pipecolic acid) | Ada-Abu | DYEPIPEEA-(Cha)-(D-Glu)-OH | 0.5–1 (N = 5) | 1–2 (N = 5) |
| P552 (SEQ ID NO:20) | TBbs-Arg-(D-Pipecolic acid) | Ada-Abu | DFEEIPEEYLQ-OH | 0.5 (N = 4) | ≧2 (N = 4) |
| P553 (SEQ ID NO:47) | TBbs-Arg-(D-Pipecolic acid) | Ada-Abu | DYEPIPEEA-(Cha)-(D-Glu)-OH | 0.25 (N = 4) | 0.5–1 (N = 4) |
| P532 (SEQ ID NO: 18) | βNas-Arg (D-Pipecolic acid) | Ada-Abu | DFEEIPEEYLQ-OH | 0.5–1 (N = 4) | 1–2 (N = 4) |
| P581 (SEQ ID NO:48) | αNas-Arg (D-Pipecolic acid) | Ada-Abu | DYEPIPEEA-(Cha)-(D-Glu)-OH | 0.5 (N = 3) | 1 (N = 3) |
| BCH-2443 (SEQ ID NO:49) | tBbs-Arg (D-Pipecolic acid) | Ada-Abu | DFEPIPY-OH | not achieved at 4 (N = 1) | Not achieved at 4 (N = 1) |
| BCH-2736 (SEQ ID NO:50) | tBbs-Arg (D-Pipecolic acid) | Ada-Abu | DFEPIPY-OH | 4 (N = 2) | Not achieved at 4 (N = 2) |
| BCH-2741 (SEQ ID NO:51) | tBbs-Arg (D-Pipecolic acid) | Ada-Abu | DFEPIPY-OH | not tested due to insolubility | |
| BCH-2733 (SEQ ID NO:52) | BrBs-Arg (D-Pipecolic acid) | Ada-Abu | DFEPIPY-OH | not achieved at 2 (N = 4) | Not achieved at 2 (N = 4) |
| BCH-2444 (SEQ ID NO:53) | tipBs-Arg (D-Pipecolic acid) | Ada-Abu | DFEPIPY-OH | not tested due to insolubility | |
| Hirulog ™ | | | | 2 (N = 4) | 4 (N = 4) |
| Heparin | | | | 200 U/Kg (N = 4) | not achieved at 400 U/Kg (N = 4) |

[1]control occlusion time is 19 ± 1 min (N = 11)
[2]as defined by no drop in vessel temperature

What is claimed is:

1. A compound of formula (II):

AS—Z—P    (II)

wherein,

AS is an active site portion,

Z is a linker portion,

P is a fibrinogen recognition exosite portion, wherein:

the active site portion (AS) is selected from the group consisting of benzyl sulfonyl-Arg-(D-pipecolic); dansyl-Arg-(D-pipecolic); dansyl-Arg-(L-pipecolic); dansyl-Nle-(D-pipecolic); (D-Phe)-Arg-(D-pipecolic); 9-fluorenylmethoxycarbonyl-Arg-(D-pipecolic); dansyl-Arg-(D)-1,2,3,4-tetrahydroisoquinoline-3-carboxylic acid); dansyl-(D-Arg)-(D-pipecolic); dansyl-Phe-(D-pipecolic); dansyl-(β-cyclohexylalanine)-(D-pipecolic); (D-β-cyclohexylalanine)-Arg-(D-pipecolic); α-naphthyl sulfonyl-Arg-(D-pipecolic); P-naphthyl sulfonyl-Arg-(D-pipecolic); 4-tert-Butyl-benzene sulfonyl-Arg-(D-Pipecolic); dansyl-Arg-(D-cyclohehexylalanine); dansyl-Arg-Acha; phenyl ethyl sulfonyl-Arg-(D-pipecolic); β-dihydroanthracenyl-β-sulfonyl-Arg-(D-pipecolic); (+)-camphorsulfonyl-Arg-(D-pipecolic); 4-bromobenzenesulfonyl-Arg-(D-pipecolic); (D)-1,2,3,4-tetrahydroisoquinoline-3-carboxylate-Arg-(D-pipecolic); and 2,4,6 triisopropylbenzenesulfonyl-Arg-(D-pipecolic);

the linker portion (Z) is selected from the group consisting of (12-aminododecanoic acid)-4-aminobutyric acid)-; (12-aminododecanoic acid)-6-aminocaproic acid); (8-aminocapylic acid)-4-aminobutyric acid)-; (12-aminododecanoic acid)-asparagyl-glycyl); (4-aminobutyric acid-glycyl); (5-amino valeric acid)-glycyl); (6-aminocaproic acid)-glycyl); (7-aminoheptanoic acid)-glycyl);(8-aminocapylic acid)-glycyl); (12-aminododecanoic acid); (11-aminoundecanoic acid)-glycyl); (Glycyl)-12-aminododecanoic acid); (12-aminododecanoic acid)-glycyl); and (β-Alanyl-glycyl-glycyl-5-aminovaleric acid (SEQ ID NO:3)); and the fibrinogen recognition exosite portion (P) is selected from the group consisting of Asp-Phe-Glu-Glu-Ile-Pro-Glu-Glu-Tyr-Leu-Gln-OH (SEQ ID NO:55); Asp-Tyr-Glu-Pro-Ile-Pro-Glu-Glu-Ala-(L-β-cyclohexylalanine)-(D-Glu)-OH (SEQ ID NO:56); and Asp-Phe-Glu-Pro-Ile-Pro-Tyr-OH (SEQ ID NO:57).

2. A compound according to claim 1 wherein said compound is selected from the group consisting of:

dansyl-Arg-(D-pipecolic acid)-(12-aminododecanoic acid)-4-aminobutyric acid)-Asp-Phe-Glu-Glu-Ile-Pro-Glu-Glu-Tyr-Leu-Gln-OH (P448) (SEQ ID NO:8);

dansyl-Arg-(L-pipecolic acid)-(12-aminododecanoic acid)-4-aminobutyric acid)-Asp-Phe-Glu-Glu-Ile-Pro-Glu-Glu-Tyr-Leu-Gln-OH (P447) (SEQ ID NO:9);

dansyl-Nle-(D-Pipecolic acid)-(12-aminododecanoic acid)-4-aminobutyric acid)-Asp-Phe-Glu-Glu-Ile-Pro-Glu-Glu-Tyr-Leu-Gln-OH (P493) (SEQ ID NO:10);

dansyl-Arg-1,2,3,4-tetrahydroisoquinoline-3-carboxylic acid-(12-aminododecanoic acid)-4-aminobutyric acid)-Asp-Phe-Glu-Glu-Ile-Pro-Glu-Glu-Tyr-Leu-Gln-OH (P471) (SEQ ID NO:11);

dansyl-Arg-(D-β-cyclohexylalanine)-(12-aminododecanoic acid)-4-aminobutyric acid)-Asp-Phe-Glu-Glu-Ile-Pro-Glu-Glu-Tyr-Leu-Gln-OH (P472) (SEQ ID NO:12);

dansyl-Arg-(D)1-amino cyclohexane carboxylic acid-(12-aminododecanoic acid)-4-aminobutyric acid)-Asp-Phe-Glu-Glu-Ile-Pro-Glu-Glu-Tyr-Leu-Gln-OH (P473) (SEQ ID NO:13);

dansyl-(D-Arg)-(D-Pipecolic acid)-(12-aminododecanoic acid)-4-aminobutyric acid)-Asp-Phe-Glu-Glu-Ile-Pro-Glu-Glu-Tyr-Leu-Gln-OH (P492) (SEQ ID NO:14);

dansyl-Phe-(D-Pipecolic acid)-(12-aminododecanoic acid)-4-aminobutyric acid)-Asp-Phe-Glu-Glu-Ile-Pro-Glu-Glu-Tyr-Leu-Gln-OH (P476) (SEQ ID NO:15);

dansyl-(β-cyclohexylalanine)-(D-Pipecolic acid)-(12-aminododecanoic acid)-4-aminobutyric acid)-Asp-Phe-Glu-Glu-Ile-Pro-Glu-Glu-Tyr-Leu-Gln-OH (P477) (SEQ ID NO:16);

α-naphthyl sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P531) (SEQ ID NO:17);

β-naphthyl sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P532) (SEQ ID NO:18);

benzyl sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P556) (SEQ ID NO:19);

4-tert-Butyl-benzene sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P552) (SEQ ID NO:20);

(+) 10-camphorsulfonyl-Arg-(D-Pipecolic acid)-(12-aminododecanoic acid)-6-aminocaproic acid-Asp-Phe-Glu-Glu-Ile-Pro-Glu-Glu-Tyr-Leu-Gln-OH (P534) (SEQ ID NO:21);

4-tert-Butyl-benzene sulfonyl-Arg-(D-Pipecolic acid)-(12-aminododecanoic acid)-6-aminocaproic acid-Asp-Phe-Glu-Glu-Ile-Pro-Glu-Glu-Tyr-Leu-Gln-OH (P540) (SEQ ID NO:22);

(D-β-cyclohexylalanine)-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P481) (SEQ ID NO:23);

(D)-1,2,3,4-tetrahydroisoquinoline-3-carboxylic acid-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P482) (SEQ ID NO:24);

(D-Phe)-Arg-(D-Pipecolic acid)(12-aminododecanoic acid)-4-aminobutyric acid)-Asp-Phe-Glu-Glu-Ile-Pro-Glu-Glu-Tyr-Leu-Gln-OH (P483) (SEQ ID NO:25);

fmoc-Arg-(D-Pipecolic acid)(12-aminododecanoic acid)-4-aminobutyric acid)-Asp-Phe-Glu-Glu-Ile-Pro-Glu-Glu-Tyr-Leu-Gln-OH (P484) (SEQ ID NO:26);

dansyl-Arg-(D-Pipecolic acid)-(4-aminobutyric acid)-glycyl)-Asp-Phe-Glu-Glu-Ile-Pro-Glu-Glu-Tyr-Leu-Gln-OH (P514) (SEQ ID NO:27);

dansyl-Arg-(D-Pipecolic acid)-(5-amino valeric acid)-glycyl)-Asp-Phe-Glu-Glu-Ile-Pro-Glu-Glu-Tyr-Leu-Gln-OH (P526) (SEQ ID NO:28);

dansyl-Arg-(D-Pipecolic acid)-(6-aminocaproic acid)-glycyl)-Asp-Phe-Glu-Glu-Ile-Pro-Glu-Glu-Tyr-Leu-Gln-OH (P525) (SEQ ID NO:29);

dansyl-Arg-(D-Pipecolic acid)-(7-aminoheptanoic acid)-glycyl)-Asp-Phe-Glu-Glu-Ile-Pro-Glu-Glu-Tyr-Leu-Gln-OH (P524) (SEQ ID NO:30);

dansyl-Arg-(D-Pipecolic acid)-(8-aminocapylic acid)-glycyl)-Asp-Phe-Glu-Glu-Ile-Pro-Glu-Glu-Tyr-Leu-Gln-OH (P523) (SEQ ID NO:31);

dansyl-Arg-(D-Pipecolic acid)-(12-aminododecanoic acid)-Asp-Phe-Glu-Glu-Ile-Pro-Glu-Glu-Tyr-Leu-Gln-OH (P499) (SEQ ID NO:32);

dansyl-Arg-(D-Pipecolic acid)-(8-aminocaproicacid)-4-aminobutyric acid)-Asp-Phe-Glu-Glu-Ile-Pro-Glu-Glu-Tyr-Leu-Gln-OH (P528) (SEQ ID NO:33);

dansyl-Arg-(D-Pipecolic acid)-(11-aminoundecanoic acid)-glycyl)-Asp-Phe-Glu-Glu-Ile-Pro-Glu-Glu-Tyr-Leu-Gln-OH (P527) (SEQ ID NO:34);

dansyl-Arg-(D-Pipecolic acid)-(Glycyl)-12-aminododecanoic acid)-Asp-Phe-Glu-Glu-Ile-Pro-Glu-Glu-Tyr-Leu-Gln-OH (P501) (SEQ ID NO:35);

dansyl-Arg-(D-Pipecolic acid)-(12-aminododecanoic acid)-glycyl)-Asp-Phe-Glu-Glu-Ile-Pro-Glu-Glu-Tyr-Leu-Gln-OH)(P500) (SEQ ID NO:36);

dansyl-Arg-(D-Pipecolic acid)-(β-Alanyl-glycyl-glycyl-5-aminovaleric acid)-Asp-Phe-Glu-Glu-Ile-Pro-Glu-Glu-Tyr-Leu-Gln-OH (P498) (SEQ ID NO:37);

dansyl-Arg-(D-Pipecolic acid)-(6-aminocaproic acid-12-aminododecanoic acid)-Asp-Phe-Glu-Glu-Ile-Pro-Glu-Glu-Tyr-Leu-Gln-OH (P513) (SEQ ID NO:38);

dansyl-Arg-(L-Pip)-(4-aminobutyric acid-glycyl)-Asp-Phe-Glu-Glu-Ile-Pro-Glu-Glu-Tyr-Leu-Gln-OH (P409) (SEQ ID NO:39);

dansyl-Arg-(L-Pip)-(5-Aminovaleric acid)-glycyl)-Asp-Phe-Glu-Glu-Ile-Pro-Glu-Glu-Tyr-Leu-Gln-OH (P547) (SEQ ID NO:40);

dansyl-Arg-(L-Pip)-(6-aminocaproic acid)-glycyl)-Asp-Phe-Glu-Glu-Ile-Pro-Glu-Glu-Tyr-Leu-Gln-OH (P408) (SEQ ID NO:41);

dansyl-Arg-(L-Pip)-(7-aminoheptanoic acid)-glycyl)-Asp-Phe-Glu-Glu-Ile-Pro-Glu-Glu-Tyr-Leu-Gln-OH (P548) (SEQ ID NO:42);

dansyl-Arg-(L-Pip)-(12-aminododecanoic acid)-Asp-Phe-Glu-Glu-Ile-Pro-Glu-Glu-Tyr-Leu-Gln-OH (P550) (SEQ ID NO:43);

dansyl-Arg-(L-pipecolic acid)-(12-aminododecanoic acid)-4-aminobutyric acid)-Asp-Phe-Glu-Glu-Ile-Pro-Glu-Glu-Tyr-Leu-Gln-OH (P447) (SEQ ID NO:44);

dansyl-Arg-(D-pipecolic acid)-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P535) (SEQ ID NO:45);

β-naphthyl sulfonyl-arginyl D-pipecolic acid-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P551) (SEQ ID NO:46);

-4-tert-butylbenzenesulfonyl-Arg-(D-pipecolic acid)-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P553) (SEQ ID NO:47);

α-naphthyl sulfonyl-arginyl D-pipecolic acid-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P581) (SEQ ID NO:48);

tert-butylbezenesulfonyl-Arg (D-Pipecolic acid)-(12-aminododecanoic acid)-4-aminobutyric acid)-Asp-Phe-Glu-Pro-Ile-Pro-Tyr-OH (BCH-2443) (SEQ ID NO:49);

tert-butylbezenesulfonyl-Arg (D-Pipecolic acid)-(12-aminododecanoic acid)-4-aminobutyric acid)-Asp-Phe-Glu-Pro-Ile-Pro-Tyr-OH (BCH-2736) (SEQ ID NO:50);

tert-butylbezenesulfonyl-Arg (D-Pipecolic acid)-(12-aminododecanoic acid)-4-aminobutyric acid)-Asp-Phe-Glu-Pro-Ile-Pro-Tyr-OH (BCH-2741) (SEQ ID NO:51);

4-bromobenzenesulfonyl-Arg (D-Pipecolic acid)-(12-aminododecanoic acid)-4-aminobutyric acid)-Asp-Phe-Glu-Pro-Ile-Pro-Tyr-OH (BCH-2733) (SEQ ID NO:52); and 2,4,6 triisopropylbenzensulfonyl-Arg (D-Pipecolic acid)-(12-aminododecanoic acid)-4-aminobutyric acid)-Asp-Phe-Glu-Pro-Ile-Pro-Tyr-OH (BCH-2444) (SEQ ID NO:53).

3. A compound according to claim 1 wherein said compound is selected from the group consisting of: dansyl-Arg-(D-pipecolic acid)-(12-aminododecanoic acid)-4-aminobutyric acid)-Asp-Phe-Glu-Glu-Ile-Pro-Glu-Glu-Tyr-Leu-Gln-OH (P448) (SEQ. ID No:8); dansyl-Arg-1,2,3,4-tetrahydroisoquinoline-3-carboxylic acid-(12-aminododecanoic acid)-4-aminobutyric acid)-Asp-Phe-Glu-Glu-Ile-Pro-Glu-Glu-Tyr-Leu-Gln-OH (P471) (SEQ. ID No.11); α-naphthyl sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH(P531) (SEQ. ID NO.17); β-naphthyl sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P532) (SEQ. ID NO.18); 4-tert-Butyl-benzene sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH(P552) (SEQ. ID. NO.20); benzyl sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH(P556) (SEQ ID. NO.19);4-tert-Butyl-benzene sulfonyl-Arg-(D Pipecolic acid)-(12-aminododecanoic acid)-6-aminocaproic acid-Asp-Phe-Glu-Glu-Ile-Pro-Glu-Glu-Tyr-Leu-Gln-OH (P540) (SEQ ID. NO. 22); (+)10-camphorsulfonyl-Arg-(D-

Pipecolic acid)-(12-aminododecanoic acid)-6-aminocaproic acid-Asp-Phe-Glu-Glu-Ile-Pro-Glu-Glu-Tyr-Leu-Gln-OH (P534) (SEQ. ID NO.21); dansyl-Arg-(D-Pipecolic acid)-(8-aminocaproic acid)-4-aminobutyric acid)-Asp-Phe-Glu-Glu-Ile-Pro-Glu-Glu-Tyr-Leu-Gln-OH (P528) (SEQ, ID. NO.33); dansyl-Arg-(D-Pipecolic acid)-(11-aminoundecanoic acid)-glycyl-Asp-Phe-Glu-Glu-Ile-Pro-Glu-Glu-Tyr-Leu-Gln-OH (P527) (SEQ. ID. NO. 34); dansyl-Arg-(D-Pipecolic acid)-(12-aminododecanoic acid)-glycyl)-Asp-Phe-Glu-Glu-Ile-Pro-Glu-Glu-Tyr-Leu-Gln-OH)(P500) (SEQ. ID. NO.36); dansyl-Arg-(D-Pipecolic acid)-(Glycyl)-12-aminododecanoic acid)-Asp-Phe-Glu-Glu-Ile-Pro-Glu-Glu-Tyr-Leu-Gln-OH (P501) (SEQ. ID. NO. 35); dansyl-Arg-(D-Pipecolic acid)-(β-Alanyl-glycyl-glycyl-5-aminovaleric acid)-Asp-Phe-Glu-Glu-Ile-Pro-Glu-Glu-Tyr-Leu-Gln-OH (P498) (SEQ. ID. NO. 37); dansyl-Arg-(D-Pipecolic acid)-(6-aminocaproic acid-12-aminododecanoic acid)-Asp-Phe-Glu-Glu-Ile-Pro-Glu-Glu-Tyr-Leu-Gln-OH (P513) (SEQ. ID NO. 38); dansyl-Arg-(D-pipecolic acid)-(12-aminododecanoic acid)-4-aminobutyric acid)-Asp-Tyr-Glu-Pro-Ile-Pro-Glu-Glu-Ala-(L-β-cyclohexylalamine)-(D-Glu)-OH (P535) (SEQ. ID. NO. 45); β-naphthyl sulfonyl-arginyl D-pipecolic acid-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P551) (SEQ. ID. NO. 46); α-naphthyl sulfonyl-arginyl D-pipecolic acid-(12-aminododecanoic acid)-4-aminobutyric acid)-Asp-Tyr-Glu-Pro-Ile-Pro-Glu-Glu-Ala-(L-β-cyclohexylalanine)-D-Glu)-OH (P581) (SEQ. ID. NO. 48); -4-tert-butylbenzenesulfonyl-Arg-(D-pipecolic acid)-(12-aminododecoanoic acid)-4-aminobutyric acid)-Asp-Tyr-Glu-Pro-Ile-Pro-Glu-Glu-Ala-(L-β-cyclohexylalanine)-(D-Glu)-OH (P553) (SEQ. ID. NO. 47); and 4-bromobenzenesulfonyl-Arg (D-Pipecolic acid)-(12-aminododecanoic acid)-4-aminobutyric acid)-Asp-Phe-Glu-Pro-Ile-Pro-Tyr-OH (BCH-2733) (SEQ. ID. NO. 52).

4. A compound according to claim 1 wherein said compound is selected from the group consisting of dansyl-Arg-(D-pipecolic acid)-(12-aminododecanoic acid)-4-aminobutyric acid)-Asp-Phe-Glu-Glu-Ile-Pro-Glu-Glu-Tyr-Leu-Gln-OH (P448) (SEQ. ID. NO. 8); α-naphthyl sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P531) (SEQ. ID. NO. 17); β-naphthyl sulfonyl-Arg-(D-Pipecolic acid)-12-aminododecanoic acid)-4-aminobutyric acid)-Asp-Phe-Glu-Glu-Ile-Pro-Glu-Glu-Tyr-Leu-Gln-OH (P532) (SEQ. ID. NO. 18); 4-tert-Butyl-benzene sulfonyl-Arg-(D-Pipecolic acid)-(12-aminododecanoic acid)-6-aminocaproic acid-Asp-Phe-Glu-Glu-Ile-Pro-Glu-Glu-Tyr-Leu-Gln-OH (P540) (SEQ. ID. NO. 22); 4-tert-Butyl-benzene sulfonyl-Arg-(D-Pipecolic acid)-(12-aminododecanoic acid)-4-aminobutyric acid)-Asp-Phe-Glu-Glu-Ile-Pro-Glu-Glu-Tyr-Leu-Gln-OH (P552) (SEQ. ID. NO. 20); dansyl-Arg-(D-Pipecolic acid)-(11-aminoundecanoic acid)-glycyl)-Asp-Phe-Glu-Glu-Ile-Pro-Glu-Glu-Tyr-Leu-Gln-OH (P527) (SEQ. ID. NO. 34); dansyl-Arg-(D-Pipecolic acid)-(12-aminododecanoic acid)-glycyl)-Asp-Phe-Glu-Glu-Ile-Pro-Glu-Glu-Tyr-Leu-Gln-OH) (P500) (SEQ. ID. No. 36); dansyl-Arg-(D-Pipecolic acid)-(Glycyl)-12-aminododecanoic acid)-Asp-Phe-Glu-Glu-Ile-Pro-Glu-Glu-Tyr-Leu-Gln-OH (P501) (SEQ. ID. NO. 35); dansyl-Arg-(D-Pipecolic acid)-(6-aminocaproic acid-12-aminododecanoic acid)-Asp-Phe-Glu-Glu-Ile-Pro-Glu-Glu-Tyr-Leu-Gln-OH (P513) (SEQ. ID. NO 38); dansyl-Arg-(D-pipecolic acid)-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P535) (SEQ. ID. NO. 45); β-naphthyl sulfonyl-arginyl D-pipecolic acid-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P551) (SEQ. ID. NO. 46); 4-tert-butylbenzenesulfonyl-Arg-(D-pipecolic acid)-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P553) (SEQ. ID. NO. 47); and α-naphthyl sulfonyl-arginyl D-pipecolic acid-(12-aminododecanoic acid)-4-aminobutyric acid)-Asp-Tyr-Glu-Pro-Ile-Pro-Glu-Glu-Ala-(L-β-cyclohexylalanine)-(D-Glu)-OH (P581) (SEQ. ID. NO. 48).

5. A compound according to claim 4, wherein said compound is 4-tert-butylbenzenesulfonyl-Arg-(D-pipecolic acid)-(12-aminododecanoic acid)-4-(aminobutyric acid)-Asp-Tyr-Glu-Pro-Ile-Pro-Glu-Glu-Ala-(L-β-cyclohexylalanine)-(D-Glu)-OH (P553) (SEQ. ID. NO. 47).

6. A pharmaceutical composition comprising a compound as defined in claim 2; a thrombolytic agent; and a pharmaceutically acceptable carrier.

7. A pharmaceutically acceptable combination for treating vascular disease in a mammal, comprising a compound as defined in claim 2; a thrombolytic agent; and a pharmaceutically acceptable carrier.

8. The combination according to claim 7 wherein said thrombolytic agent is tissue plasminogen activator.

9. A pharmaceutical composition comprising a compound as defined in claim 1 in an amount effective for treating vascular disease in a mammal and, a pharmaceutically acceptable carrier.

10. A pharmaceutically acceptable combination for treating vascular diseases in a mammal, comprising a compound as defined in claim 1; a thrombolytic agent; and a pharmaceutically acceptable carrier.

11. A method for the treatment of vascular diseases of a mammal, comprising the administration to a mammal in need thereof of an effective amount of a composition according to claim 6.

12. A method for the treatment of vascular diseases of a mammal, comprising the administration to a mammal in need thereof of an effective amount of a combination according to claim 7.

* * * * *

SEQUENCE LISTING (1) GENERAL INFORMATION:

(iii) NUMBER OF SEQUENCES: 57

(2) INFORMATION FOR SEQ ID NO:1:

(i) SEQUENCE CHARACTERISTICS:
       (A) LENGTH: 6 amino acids
       (B) TYPE: amino acid
       (C) STRANDEDNESS: single
       (D) TOPOLOGY: linear (ix) FEATURE:
       (A) NAME/KEY: Modified-site
       (B) LOCATION: 1
       (D) OTHER INFORMATION: /label= G

```
             /note= "Any independently acidic alpha-amino acid
             residue"

(ix) FEATURE:
        (A) NAME/KEY: Modified-site
        (B) LOCATION: 2
        (D) OTHER INFORMATION: /label= X2
             /note= "Any hydrophobic alpha-amino acid residue"

(ix) FEATURE:
        (A) NAME/KEY: Modified-site
        (B) LOCATION: 3
        (D) OTHER INFORMATION: /label= G1
             /note= "Any independently acidic alpha-amino acid
             residue"

(ix) FEATURE:
        (A) NAME/KEY: Modified-site
        (B) LOCATION: 4
        (D) OTHER INFORMATION: /label= Q
             /note= "If present, residue is derived from an
             L-alpha-amino
             acid or a cyclic imino acid"

(ix) FEATURE:
        (A) NAME/KEY: Modified-site
        (B) LOCATION: 5
        (D) OTHER INFORMATION: /label= X3
             /note= "If present, residue is any hydrophobic
             alpha-amino acid"

(ix) FEATURE:
        (A) NAME/KEY: Modified-site
        (B) LOCATION: 6
        (D) OTHER INFORMATION: /label= R2
             /note= "A hydrophobic oligopeptide having all or
             a portion of SEQ ID NO:4"

(ix) FEATURE:
        (A) NAME/KEY: Region
        (B) LOCATION: 1..6
        (D) OTHER INFORMATION: /note= "Consists of at least 6
             amino or imino acid residues"

(xi) SEQUENCE DESCRIPTION: SEQ ID NO:1:

Xaa Xaa Xaa Xaa Xaa Xaa
1               5

(2) INFORMATION FOR SEQ ID NO:2:

(i) SEQUENCE CHARACTERISTICS:
        (A) LENGTH: 6 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 4
        (D) OTHER INFORMATION: /label= V
             /note= "Any independently hydrophobic amino acid
             residue"

(ix) FEATURE:
        (A) NAME/KEY: Modified-site
        (B) LOCATION: 5
        (D) OTHER INFORMATION: /label= W
             /note= "Any independently hydrophobic amino acid
             residue"

(ix) FEATURE:
        (A) NAME/KEY: Modified-site
        (B) LOCATION: 6
        (D) OTHER INFORMATION: /label= X
             /note= "Either D-Glu, L-Glu or Gln"

(xi) SEQUENCE DESCRIPTION: SEQ ID NO:2:
```

```
Pro Glu Glu Xaa Xaa Xaa
1               5
```

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /product= "bAla"

(ix) FEATURE:
        (A) NAME/KEY: Modified-site
        (B) LOCATION: 4
        (D) OTHER INFORMATION: /product= "OTHER"
            /note= "5-aminovaleric acid"

(xi) SEQUENCE DESCRIPTION: SEQ ID NO:3:

```
Xaa Gly Gly Xaa
1
```

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: group(4, 5)
        (D) OTHER INFORMATION: /label= V-W
            /note= "Any of the following residues: Tyr-Leu, Tyr-Ala,
            Tyr-(beta-cyclohexylalanine),
            (beta-Cyclohexylalanine)-Leu,
            Pro-Tyr, Ala-(beta-cyclohexylalanine), Phe-Tyr or
            (beta-cyclohexylalanine)-Ala"

(ix) FEATURE:
        (A) NAME/KEY: Modified-site
        (B) LOCATION: 6
        (D) OTHER INFORMATION: /label= X
            /note= "Either D-Glu or Gln"

(xi) SEQUENCE DESCRIPTION: SEQ ID NO:4:

```
Pro Glu Glu Xaa Xaa Xaa
1               5
```

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:5:

```
Asp Phe Glu Glu Ile Pro Glu Glu Tyr Leu Gln
1               5                   10
```

(2) INFORMATION FOR SEQ ID NO:6:

(i) SEQUENCE CHARACTERISTICS:
        (A) LENGTH: 11 amino acids
        (B) TYPE: amino acid

```
            (C) STRANDEDNESS: single
            (D) TOPOLOGY: linear (ix) FEATURE:
            (A) NAME/KEY: Modified-site
            (B) LOCATION: 10
            (D) OTHER INFORMATION: /product= "OTHER"
                /note= "L-beta-cyclohexylalanine"

(ix) FEATURE:
            (A) NAME/KEY: Modified-site
            (B) LOCATION: 11
            (D) OTHER INFORMATION: /product= "OTHER"
                /note= "D-Glu"

(xi) SEQUENCE DESCRIPTION: SEQ ID NO:6:

Asp Tyr Glu Pro Ile Pro Glu Glu Ala Xaa Xaa
1               5                   10

(2) INFORMATION FOR SEQ ID NO:7:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO:7:

Asp Phe Glu Pro Ile Pro Tyr
1               5

(2) INFORMATION FOR SEQ ID NO:8:

(i) SEQUENCE CHARACTERISTICS:
            (A) LENGTH: 15 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION: /note= "dansyl group attached"

(ix) FEATURE:
            (A) NAME/KEY: Modified-site
            (B) LOCATION: 2
            (D) OTHER INFORMATION: /product= "OTHER"
                /note= "D-pipecolic acid"

(ix) FEATURE:
            (A) NAME/KEY: Modified-site
            (B) LOCATION: 3
            (D) OTHER INFORMATION: /product= "OTHER"
                /note= "12-aminododecanoic acid"

(ix) FEATURE:
            (A) NAME/KEY: Modified-site
            (B) LOCATION: 4
            (D) OTHER INFORMATION: /product= "4Abu"

(ix) FEATURE:
            (A) NAME/KEY: Peptide
            (B) LOCATION: 1..15
            (D) OTHER INFORMATION: /label= P448

(xi) SEQUENCE DESCRIPTION: SEQ ID NO:8:

Arg Xaa Xaa Xaa Asp Phe Glu Glu Ile Pro Glu Glu Tyr Leu Gln
1               5                   10                  15

(2) INFORMATION FOR SEQ ID NO:9:

(i) SEQUENCE CHARACTERISTICS:
```

(A) LENGTH: 15 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "dansyl group attached"

(ix) FEATURE:
        (A) NAME/KEY: Modified-site
        (B) LOCATION: 2
        (D) OTHER INFORMATION: /product= "OTHER"
            /note= "L-pipecolic acid"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Modified-site
        (B) LOCATION: 4
        (D) OTHER INFORMATION: /product= "4Abu"

(ix) FEATURE:
        (A) NAME/KEY: Peptide
        (B) LOCATION: 1..15
        (D) OTHER INFORMATION: /label= P447

(xi) SEQUENCE DESCRIPTION: SEQ ID NO:9:

Arg Xaa Xaa Xaa Asp Phe Glu Glu Ile Pro Glu Glu Tyr Leu Gln
 1               5                  10                  15

(2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /product= "Nle"
            /note= "dansyl group attached"

(ix) FEATURE:
        (A) NAME/KEY: Modified-site
        (B) LOCATION: 2
        (D) OTHER INFORMATION: /product= "OTHER"
            /note= "D-pipecolic acid"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Modified-site
        (B) LOCATION: 4
        (D) OTHER INFORMATION: /product= "4Abu"

(ix) FEATURE:
        (A) NAME/KEY: Peptide
        (B) LOCATION: 1..15
        (D) OTHER INFORMATION: /label= P493

(xi) SEQUENCE DESCRIPTION: SEQ ID NO:10:

Xaa Xaa Xaa Xaa Asp Phe Glu Glu Ile Pro Glu Glu Tyr Leu Gln
 1               5                  10                  15

(2) INFORMATION FOR SEQ ID NO:11:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "dansyl group attached"

(ix) FEATURE:
        (A) NAME/KEY: Modified-site
        (B) LOCATION: 2
        (D) OTHER INFORMATION: /product= "OTHER"
            /note= "1,2,3,4-tetrahydroisoquinoline-3-carboxylic acid"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Modified-site
        (B) LOCATION: 4
        (D) OTHER INFORMATION: /product= "4Abu"

(ix) FEATURE:
        (A) NAME/KEY: Peptide
        (B) LOCATION: 1..15
        (D) OTHER INFORMATION: /label= P471

(xi) SEQUENCE DESCRIPTION: SEQ ID NO:11:

Arg Xaa Xaa Xaa Asp Phe Glu Glu Ile Pro Glu Glu Tyr Leu Gln
1               5                   10                  15

(2) INFORMATION FOR SEQ ID NO:12:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "dansyl group attached"

(ix) FEATURE:
        (A) NAME/KEY: Modified-site
        (B) LOCATION: 2
        (D) OTHER INFORMATION: /product= "OTHER"
            /note= "D-beta-cyclohexylalanine"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Modified-site
        (B) LOCATION: 4
        (D) OTHER INFORMATION: /product= "4Abu"

(ix) FEATURE:
        (A) NAME/KEY: Peptide
        (B) LOCATION: 1..15
        (D) OTHER INFORMATION: /label= P472

(xi) SEQUENCE DESCRIPTION: SEQ ID NO:12:

```
Arg Xaa Xaa Xaa Asp Phe Glu Glu Ile Pro Glu Glu Tyr Leu Gln
1               5                   10                  15
```

(2) INFORMATION FOR SEQ ID NO:13:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "dansyl group attached"

(ix) FEATURE:
        (A) NAME/KEY: Modified-site
        (B) LOCATION: 2
        (D) OTHER INFORMATION: /product= "OTHER"
            /note= "(D)1-amino cyclohexane carboxylic acid"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Modified-site
        (B) LOCATION: 4
        (D) OTHER INFORMATION: /product= "4Abu"

(ix) FEATURE:
        (A) NAME/KEY: Peptide
        (B) LOCATION: 1..15
        (D) OTHER INFORMATION: /label= P473

(xi) SEQUENCE DESCRIPTION: SEQ ID NO:13:

```
Arg Xaa Xaa Xaa Asp Phe Glu Glu Ile Pro Glu Glu Tyr Leu Gln
1               5                   10                  15
```

(2) INFORMATION FOR SEQ ID NO:14:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /product= "OTHER"
            /note= "D-Arg; dansyl group attached"

(ix) FEATURE:
        (A) NAME/KEY: Modified-site
        (B) LOCATION: 2
        (D) OTHER INFORMATION: /product= "OTHER"
            /note= "D-pipecolic acid"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Modified-site
        (B) LOCATION: 4
        (D) OTHER INFORMATION: /product= "4Abu"

(ix) FEATURE:
        (A) NAME/KEY: Peptide
        (B) LOCATION: 1..15

(D) OTHER INFORMATION: /label= P492

(xi) SEQUENCE DESCRIPTION: SEQ ID NO:14:

Xaa Xaa Xaa Xaa Asp Phe Glu Glu Ile Pro Glu Glu Tyr Leu Gln
1               5                   10                  15

(2) INFORMATION FOR SEQ ID NO:15:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "dansyl group attached"

(ix) FEATURE:
        (A) NAME/KEY: Modified-site
        (B) LOCATION: 2
        (D) OTHER INFORMATION: /product= "OTHER"
            /note= "D-pipecolic acid"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Modified-site
        (B) LOCATION: 4
        (D) OTHER INFORMATION: /product= "4Abu"

(ix) FEATURE:
        (A) NAME/KEY: Peptide
        (B) LOCATION: 1..15
        (D) OTHER INFORMATION: /label= P476

(xi) SEQUENCE DESCRIPTION: SEQ ID NO:15:

Phe Xaa Xaa Xaa Asp Phe Glu Glu Ile Pro Glu Glu Tyr Leu Gln
1               5                   10                  15

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /product= "OTHER"
            /note= "beta-cyclohexylalanine; dansyl group attached"

(ix) FEATURE:
        (A) NAME/KEY: Modified-site
        (B) LOCATION: 2
        (D) OTHER INFORMATION: /product= "OTHER"
            /note= "D-pipecolic acid"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Modified-site
        (B) LOCATION: 4
        (D) OTHER INFORMATION: /product= "4Abu"

-continued

```
    (ix) FEATURE:
         (A) NAME/KEY: Peptide
         (B) LOCATION: 1..15
         (D) OTHER INFORMATION: /label= P477

(xi) SEQUENCE DESCRIPTION: SEQ ID NO:16:

Xaa Xaa Xaa Xaa Asp Phe Glu Glu Ile Pro Glu Glu Tyr Leu Gln
1               5                   10                  15

(2) INFORMATION FOR SEQ ID NO:17:

(i) SEQUENCE CHARACTERISTICS:
         (A) LENGTH: 15 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 1
         (D) OTHER INFORMATION: /note= "alpha-naphthyl sulfonyl
             group attached"

(ix) FEATURE:
         (A) NAME/KEY: Modified-site
         (B) LOCATION: 2
         (D) OTHER INFORMATION: /product= "OTHER"
             /note= "D-pipecolic acid"

(ix) FEATURE:
         (A) NAME/KEY: Modified-site
         (B) LOCATION: 3
         (D) OTHER INFORMATION: /product= "OTHER"
             /note= "12-aminododecanoic acid"

(ix) FEATURE:
         (A) NAME/KEY: Modified-site
         (B) LOCATION: 4
         (D) OTHER INFORMATION: /product= "4Abu"

(ix) FEATURE:
         (A) NAME/KEY: Peptide
         (B) LOCATION: 1..15
         (D) OTHER INFORMATION: /label= P531

(xi) SEQUENCE DESCRIPTION: SEQ ID NO:17:

Arg Xaa Xaa Xaa Asp Phe Glu Glu Ile Pro Glu Glu Tyr Leu Gln
1               5                   10                  15

(2) INFORMATION FOR SEQ ID NO:18:

(i) SEQUENCE CHARACTERISTICS:
         (A) LENGTH: 15 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 1
         (D) OTHER INFORMATION: /note= "beta-naphthyl sulfonyl
             group attached"

(ix) FEATURE:
         (A) NAME/KEY: Modified-site
         (B) LOCATION: 2
         (D) OTHER INFORMATION: /product= "OTHER"
             /note= "D-pipecolic acid"

(ix) FEATURE:
         (A) NAME/KEY: Modified-site
         (B) LOCATION: 3
         (D) OTHER INFORMATION: /product= "OTHER"
             /note= "12-aminododecanoic acid"
```

```
     (ix) FEATURE:
           (A) NAME/KEY: Modified-site
           (B) LOCATION: 4
           (D) OTHER INFORMATION: /product= "4Abu"

(ix) FEATURE:
           (A) NAME/KEY: Peptide
           (B) LOCATION: 1..15
           (D) OTHER INFORMATION: /label= P532

(xi) SEQUENCE DESCRIPTION: SEQ ID NO:18:

Arg Xaa Xaa Xaa Asp Phe Glu Glu Ile Pro Glu Glu Tyr Leu Gln
1               5                   10                  15

(2) INFORMATION FOR SEQ ID NO:19:

(i) SEQUENCE CHARACTERISTICS:
           (A) LENGTH: 15 amino acids
           (B) TYPE: amino acid
           (C) STRANDEDNESS: single
           (D) TOPOLOGY: linear (ix) FEATURE:
           (A) NAME/KEY: Modified-site
           (B) LOCATION: 1
           (D) OTHER INFORMATION: /note= "benzyl sulfonyl group
               attached"

(ix) FEATURE:
           (A) NAME/KEY: Modified-site
           (B) LOCATION: 2
           (D) OTHER INFORMATION: /product= "OTHER"
               /note= "D-pipecolic acid"

(ix) FEATURE:
           (A) NAME/KEY: Modified-site
           (B) LOCATION: 3
           (D) OTHER INFORMATION: /product= "OTHER"
               /note= "12-aminododecanoic acid"

(ix) FEATURE:
           (A) NAME/KEY: Modified-site
           (B) LOCATION: 4
           (D) OTHER INFORMATION: /product= "4Abu"

(ix) FEATURE:
           (A) NAME/KEY: Peptide
           (B) LOCATION: 1..15
           (D) OTHER INFORMATION: /label= P556

(xi) SEQUENCE DESCRIPTION: SEQ ID NO:19:

Arg Xaa Xaa Xaa Asp Phe Glu Glu Ile Pro Glu Glu Tyr Leu Gln
1               5                   10                  15

(2) INFORMATION FOR SEQ ID NO:20:

(i) SEQUENCE CHARACTERISTICS:
           (A) LENGTH: 15 amino acids
           (B) TYPE: amino acid
           (C) STRANDEDNESS: single
           (D) TOPOLOGY: linear (ix) FEATURE:
           (A) NAME/KEY: Modified-site
           (B) LOCATION: 1
           (D) OTHER INFORMATION: /note= "4-tert-butyl-benzene
               sulfonyl group attached"

(ix) FEATURE:
           (A) NAME/KEY: Modified-site
           (B) LOCATION: 2
           (D) OTHER INFORMATION: /product= "OTHER"
               /note= "D-pipecolic acid"
```

```
    (ix) FEATURE:
         (A) NAME/KEY: Modified-site
         (B) LOCATION: 3
         (D) OTHER INFORMATION: /product= "OTHER"
             /note= "12-aminododecanoic acid"

(ix) FEATURE:
         (A) NAME/KEY: Modified-site
         (B) LOCATION: 4
         (D) OTHER INFORMATION: /product= "4Abu"

(ix) FEATURE:
         (A) NAME/KEY: Peptide
         (B) LOCATION: 1..15
         (D) OTHER INFORMATION: /label= P552

(xi) SEQUENCE DESCRIPTION: SEQ ID NO:20:

Arg Xaa Xaa Xaa Asp Phe Glu Glu Ile Pro Glu Glu Tyr Leu Gln
 1               5                  10                  15

(2) INFORMATION FOR SEQ ID NO:21:

(i) SEQUENCE CHARACTERISTICS:
         (A) LENGTH: 15 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 1
         (D) OTHER INFORMATION: /note= "(+) 10-camphorsulfonyl
             group attached"

(ix) FEATURE:
         (A) NAME/KEY: Modified-site
         (B) LOCATION: 2
         (D) OTHER INFORMATION: /product= "OTHER"
             /note= "D-pipecolic acid"

(ix) FEATURE:
         (A) NAME/KEY: Modified-site
         (B) LOCATION: 3
         (D) OTHER INFORMATION: /product= "OTHER"
             /note= "12-aminododecanoic acid"

(ix) FEATURE:
         (A) NAME/KEY: Modified-site
         (B) LOCATION: 4
         (D) OTHER INFORMATION: /product= "Acp"

(ix) FEATURE:
         (A) NAME/KEY: Peptide
         (B) LOCATION: 1..15
         (D) OTHER INFORMATION: /label= P534

(xi) SEQUENCE DESCRIPTION: SEQ ID NO:21:

Arg Xaa Xaa Xaa Asp Phe Glu Glu Ile Pro Glu Glu Tyr Leu Gln
 1               5                  10                  15

(2) INFORMATION FOR SEQ ID NO:22:

(i) SEQUENCE CHARACTERISTICS:
         (A) LENGTH: 15 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 1
         (D) OTHER INFORMATION: /note= "4-tert-butyl-benzene
             sulfonyl group attached"

(ix) FEATURE:
```

```
            (A) NAME/KEY: Modified-site
            (B) LOCATION: 2
            (D) OTHER INFORMATION: /product= "OTHER"
                /note= "D-pipecolic acid"

(ix) FEATURE:
            (A) NAME/KEY: Modified-site
            (B) LOCATION: 3
            (D) OTHER INFORMATION: /product= "OTHER"
                /note= "12-aminododecanoic acid"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Peptide
            (B) LOCATION: 1..15
            (D) OTHER INFORMATION: /label= P540

(xi) SEQUENCE DESCRIPTION: SEQ ID NO:22:

Arg Xaa Xaa Xaa Asp Phe Glu Glu Ile Pro Glu Glu Tyr Leu Gln
1               5                   10                  15

(2) INFORMATION FOR SEQ ID NO:23:

(i) SEQUENCE CHARACTERISTICS:
            (A) LENGTH: 16 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION: /product= "OTHER"
                /note= "D-beta-cyclohexylalanine"

(ix) FEATURE:
            (A) NAME/KEY: Modified-site
            (B) LOCATION: 3
            (D) OTHER INFORMATION: /product= "OTHER"
                /note= "D-pipecolic acid"

(ix) FEATURE:
            (A) NAME/KEY: Modified-site
            (B) LOCATION: 4
            (D) OTHER INFORMATION: /product= "OTHER"
                /note= "12-aminododecanoic acid"

(ix) FEATURE:
            (A) NAME/KEY: Modified-site
            (B) LOCATION: 5
            (D) OTHER INFORMATION: /product= "4Abu"

(ix) FEATURE:
            (A) NAME/KEY: Peptide
            (B) LOCATION: 1..16
            (D) OTHER INFORMATION: /label= P481

(xi) SEQUENCE DESCRIPTION: SEQ ID NO:23:

Xaa Arg Xaa Xaa Xaa Asp Phe Glu Glu Ile Pro Glu Glu Tyr Leu Gln
1               5                   10                  15

(2) INFORMATION FOR SEQ ID NO:24:

(i) SEQUENCE CHARACTERISTICS:
            (A) LENGTH: 16 amino acids
            (B) TYPE: amino acid
            (C) STRANDEDNESS: single
            (D) TOPOLOGY: linear (ix) FEATURE:
            (A) NAME/KEY: Modified-site
```

(B) LOCATION: 1
    (D) OTHER INFORMATION: /product= "OTHER"
        /note= "(D)-1,2,3,4-tetrahydroisoquinoline-3-carboxylic
        acid"

(ix) FEATURE:
    (A) NAME/KEY: Modified-site
    (B) LOCATION: 3
    (D) OTHER INFORMATION: /product= "OTHER"
        /note= "D-pipecolic acid"

(ix) FEATURE:
    (A) NAME/KEY: Modified-site
    (B) LOCATION: 4
    (D) OTHER INFORMATION: /product= "OTHER"
        /note= "12-aminododecanoic acid"

(ix) FEATURE:
    (A) NAME/KEY: Modified-site
    (B) LOCATION: 5
    (D) OTHER INFORMATION: /product= "4Abu"

(ix) FEATURE:
    (A) NAME/KEY: Peptide
    (B) LOCATION: 1..16
    (D) OTHER INFORMATION: /label= P482

(xi) SEQUENCE DESCRIPTION: SEQ ID NO:24:

Xaa Arg Xaa Xaa Xaa Asp Phe Glu Glu Ile Pro Glu Glu Tyr Leu Gln
1               5                   10                  15

(2) INFORMATION FOR SEQ ID NO:25:

(i) SEQUENCE CHARACTERISTICS:
        (A) LENGTH: 16 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /product= "OTHER"
            /note= "D-Phe"

(ix) FEATURE:
        (A) NAME/KEY: Modified-site
        (B) LOCATION: 3
        (D) OTHER INFORMATION: /product= "OTHER"
            /note= "D-pipecolic acid"

(ix) FEATURE:
        (A) NAME/KEY: Modified-site
        (B) LOCATION: 4
        (D) OTHER INFORMATION: /product= "OTHER"
            /note= "12-aminododecanoic acid"

(ix) FEATURE:
        (A) NAME/KEY: Modified-site
        (B) LOCATION: 5
        (D) OTHER INFORMATION: /product= "4Abu"

(ix) FEATURE:
        (A) NAME/KEY: Peptide
        (B) LOCATION: 1..16
        (D) OTHER INFORMATION: /label= P483

(xi) SEQUENCE DESCRIPTION: SEQ ID NO:25:

Xaa Arg Xaa Xaa Xaa Asp Phe Glu Glu Ile Pro Glu Glu Tyr Leu Gln
1               5                   10                  15

(2) INFORMATION FOR SEQ ID NO:26:

(i) SEQUENCE CHARACTERISTICS:
        (A) LENGTH: 15 amino acids (B) TYPE: amino acid
                (C) STRANDEDNESS: single
                (D) TOPOLOGY: linear (ix) FEATURE:
                (A) NAME/KEY: Modified-site
                (B) LOCATION: 1
                (D) OTHER INFORMATION: /note= "9-fluorenylmethoxycarbonyl
                    group attached"

(ix) FEATURE:
                (A) NAME/KEY: Modified-site
                (B) LOCATION: 2
                (D) OTHER INFORMATION: /product= "OTHER"
                    /note= "D-pipecolic acid"

(ix) FEATURE:
                (A) NAME/KEY: Modified-site
                (B) LOCATION: 3
                (D) OTHER INFORMATION: /product= "OTHER"
                    /note= "12-aminododecanoic acid"

(ix) FEATURE:
                (A) NAME/KEY: Modified-site
                (B) LOCATION: 4
                (D) OTHER INFORMATION: /product= "4Abu"

(ix) FEATURE:
                (A) NAME/KEY: Peptide
                (B) LOCATION: 1..15
                (D) OTHER INFORMATION: /label= P484

(xi) SEQUENCE DESCRIPTION: SEQ ID NO:26:

Arg Xaa Xaa Xaa Asp Phe Glu Glu Ile Pro Glu Glu Tyr Leu Gln
1               5                   10                  15

(2) INFORMATION FOR SEQ ID NO:27:

(i) SEQUENCE CHARACTERISTICS:
                (A) LENGTH: 15 amino acids
                (B) TYPE: amino acid
                (C) STRANDEDNESS: single
                (D) TOPOLOGY: linear (ix) FEATURE:
                (A) NAME/KEY: Modified-site
                (B) LOCATION: 1
                (D) OTHER INFORMATION: /note= "dansyl group attached"

(ix) FEATURE:
                (A) NAME/KEY: Modified-site
                (B) LOCATION: 2
                (D) OTHER INFORMATION: /product= "OTHER"
                    /note= "D-pipecolic acid"

(ix) FEATURE:
                (A) NAME/KEY: Modified-site
                (B) LOCATION: 3
                (D) OTHER INFORMATION: /product= "4Abu"

(ix) FEATURE:
                (A) NAME/KEY: Peptide
                (B) LOCATION: 1..15
                (D) OTHER INFORMATION: /label= P514

(xi) SEQUENCE DESCRIPTION: SEQ ID NO:27:

Arg Xaa Xaa Gly Asp Phe Glu Glu Ile Pro Glu Glu Tyr Leu Gln
1               5                   10                  15

(2) INFORMATION FOR SEQ ID NO:28:

(i) SEQUENCE CHARACTERISTICS:
                (A) LENGTH: 15 amino acids
                (B) TYPE: amino acid
                (C) STRANDEDNESS: single

```
            (D) TOPOLOGY: linear (ix) FEATURE:
           (A) NAME/KEY: Modified-site
           (B) LOCATION: 1
           (D) OTHER INFORMATION: /note= "dansyl group attached"

(ix) FEATURE:
           (A) NAME/KEY: Modified-site
           (B) LOCATION: 2
           (D) OTHER INFORMATION: /product= "OTHER"
               /note= "D-pipecolic acid"

(ix) FEATURE:
           (A) NAME/KEY: Modified-site
           (B) LOCATION: 3
           (D) OTHER INFORMATION: /product= "OTHER"
               /note= "5-amino valeric acid"

(ix) FEATURE:
           (A) NAME/KEY: Peptide
           (B) LOCATION: 1..15
           (D) OTHER INFORMATION: /label= P526

(xi) SEQUENCE DESCRIPTION: SEQ ID NO:28:

Arg Xaa Xaa Gly Asp Phe Glu Glu Ile Pro Glu Glu Tyr Leu Gln
1               5                   10                  15

(2) INFORMATION FOR SEQ ID NO:29:

(i) SEQUENCE CHARACTERISTICS:
           (A) LENGTH: 15 amino acids
           (B) TYPE: amino acid
           (C) STRANDEDNESS: single
           (D) TOPOLOGY: linear (ix) FEATURE:
           (A) NAME/KEY: Modified-site
           (B) LOCATION: 1
           (D) OTHER INFORMATION: /note= "dansyl group attached"

(ix) FEATURE:
           (A) NAME/KEY: Modified-site
           (B) LOCATION: 2
           (D) OTHER INFORMATION: /product= "OTHER"
               /note= "D-Pipecolic acid"

(ix) FEATURE:
           (A) NAME/KEY: Modified-site
           (B) LOCATION: 3
           (D) OTHER INFORMATION: /product= "Acp"

(ix) FEATURE:
           (A) NAME/KEY: Peptide
           (B) LOCATION: 1..15
           (D) OTHER INFORMATION: /label= P525

(xi) SEQUENCE DESCRIPTION: SEQ ID NO:29:

Arg Xaa Xaa Gly Asp Phe Glu Glu Ile Pro Glu Glu Tyr Leu Gln
1               5                   10                  15

(2) INFORMATION FOR SEQ ID NO:30:

(i) SEQUENCE CHARACTERISTICS:
           (A) LENGTH: 15 amino acids
           (B) TYPE: amino acid
           (C) STRANDEDNESS: single
           (D) TOPOLOGY: linear (ix) FEATURE:
           (A) NAME/KEY: Modified-site
           (B) LOCATION: 1
           (D) OTHER INFORMATION: /note= "dansyl group attached"

(ix) FEATURE:
```

```
            (A) NAME/KEY: Modified-site
            (B) LOCATION: 2
            (D) OTHER INFORMATION: /product= "OTHER"
                /note= "D-pipecolic acid"

(ix) FEATURE:
            (A) NAME/KEY: Modified-site
            (B) LOCATION: 3
            (D) OTHER INFORMATION: /product= "OTHER"
                /note= "7-aminoheptanoic acid"

(ix) FEATURE:
            (A) NAME/KEY: Peptide
            (B) LOCATION: 1..15
            (D) OTHER INFORMATION: /label= P524

(xi) SEQUENCE DESCRIPTION: SEQ ID NO:30:

Arg Xaa Xaa Gly Asp Phe Glu Glu Ile Pro Glu Glu Tyr Leu Gln
 1               5                  10                  15

(2) INFORMATION FOR SEQ ID NO:31:

(i) SEQUENCE CHARACTERISTICS:
            (A) LENGTH: 15 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION: /note= "dansyl group attached"

(ix) FEATURE:
            (A) NAME/KEY: Modified-site
            (B) LOCATION: 2
            (D) OTHER INFORMATION: /product= "OTHER"
                /note= "D-pipecolic acid"

(ix) FEATURE:
            (A) NAME/KEY: Modified-site
            (B) LOCATION: 3
            (D) OTHER INFORMATION: /product= "OTHER"
                /note= "8-aminocapylic acid"

(ix) FEATURE:
            (A) NAME/KEY: Peptide
            (B) LOCATION: 1..15
            (D) OTHER INFORMATION: /label= P523

(xi) SEQUENCE DESCRIPTION: SEQ ID NO:31:

Arg Xaa Xaa Gly Asp Phe Glu Glu Ile Pro Glu Glu Tyr Leu Gln
 1               5                  10                  15

(2) INFORMATION FOR SEQ ID NO:32:

(i) SEQUENCE CHARACTERISTICS:
            (A) LENGTH: 14 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION: /note= "dansyl group attached"

(ix) FEATURE:
            (A) NAME/KEY: Modified-site
            (B) LOCATION: 2
            (D) OTHER INFORMATION: /product= "OTHER"
                /note= "D-pipecolic acid"

(ix) FEATURE:
            (A) NAME/KEY: Modified-site
```

```
          (B) LOCATION: 3
          (D) OTHER INFORMATION: /product= "OTHER"
               /note= "12-aminododecanoic acid"

(ix) FEATURE:
          (A) NAME/KEY: Peptide
          (B) LOCATION: 1..14
          (D) OTHER INFORMATION: /label= P499

(xi) SEQUENCE DESCRIPTION: SEQ ID NO:32:

Arg Xaa Xaa Asp Phe Glu Glu Ile Pro Glu Glu Tyr Leu Gln
1               5                   10

(2) INFORMATION FOR SEQ ID NO:33:

(i) SEQUENCE CHARACTERISTICS:
          (A) LENGTH: 15 amino acids
          (B) TYPE: amino acid
          (C) STRANDEDNESS: single
          (D) TOPOLOGY: linear (ix) FEATURE:
          (A) NAME/KEY: Modified-site
          (B) LOCATION: 1
          (D) OTHER INFORMATION: /note= "dansyl group attached"

(ix) FEATURE:
          (A) NAME/KEY: Modified-site
          (B) LOCATION: 2
          (D) OTHER INFORMATION: /product= "OTHER"
               /note= "D-pipecolic acid"

(ix) FEATURE:
          (A) NAME/KEY: Modified-site
          (B) LOCATION: 3
          (D) OTHER INFORMATION: /product= "OTHER"
               /note= "8-aminocaproic acid"

(ix) FEATURE:
          (A) NAME/KEY: Modified-site
          (B) LOCATION: 4
          (D) OTHER INFORMATION: /product= "4Abu"

(ix) FEATURE:
          (A) NAME/KEY: Peptide
          (B) LOCATION: 1..15
          (D) OTHER INFORMATION: /label= P528

(xi) SEQUENCE DESCRIPTION: SEQ ID NO:33:

Arg Xaa Xaa Xaa Asp Phe Glu Glu Ile Pro Glu Glu Tyr Leu Gln
1               5                   10                  15

(2) INFORMATION FOR SEQ ID NO:34:

(i) SEQUENCE CHARACTERISTICS:
          (A) LENGTH: 15 amino acids
          (B) TYPE: amino acid
          (C) STRANDEDNESS: single
          (D) TOPOLOGY: linear (ix) FEATURE:
          (A) NAME/KEY: Modified-site
          (B) LOCATION: 1
          (D) OTHER INFORMATION: /note= "dansyl group attached"

(ix) FEATURE:
          (A) NAME/KEY: Modified-site
          (B) LOCATION: 2
          (D) OTHER INFORMATION: /product= "OTHER"
               /note= "D-pipecolic acid"

(ix) FEATURE:
          (A) NAME/KEY: Modified-site
          (B) LOCATION: 3
          (D) OTHER INFORMATION: /product= "OTHER"
```

/note= "11-aminoundecanoic acid"

(ix) FEATURE:
         (A) NAME/KEY: Peptide
         (B) LOCATION: 1..15
         (D) OTHER INFORMATION: /label= P527

(xi) SEQUENCE DESCRIPTION: SEQ ID NO:34:

Arg Xaa Xaa Gly Asp Phe Glu Glu Ile Pro Glu Glu Tyr Leu Gln
1               5                   10                  15

(2) INFORMATION FOR SEQ ID NO:35:

(i) SEQUENCE CHARACTERISTICS:
         (A) LENGTH: 15 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 1
         (D) OTHER INFORMATION: /note= "dansyl group attached"

(ix) FEATURE:
         (A) NAME/KEY: Modified-site
         (B) LOCATION: 2
         (D) OTHER INFORMATION: /product= "OTHER"
              /note= "D-pipecolic acid"

(ix) FEATURE:
         (A) NAME/KEY: Modified-site
         (B) LOCATION: 4
         (D) OTHER INFORMATION: /product= "OTHER"
              /note= "12-aminododecanoic acid"

(ix) FEATURE:
         (A) NAME/KEY: Peptide
         (B) LOCATION: 1..15
         (D) OTHER INFORMATION: /label= P501

(xi) SEQUENCE DESCRIPTION: SEQ ID NO:35:

Arg Xaa Gly Xaa Asp Phe Glu Glu Ile Pro Glu Glu Tyr Leu Gln
1               5                   10                  15

(2) INFORMATION FOR SEQ ID NO:36:

(i) SEQUENCE CHARACTERISTICS:
         (A) LENGTH: 15 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 1
         (D) OTHER INFORMATION: /note= "dansyl group attached"

(ix) FEATURE:
         (A) NAME/KEY: Modified-site
         (B) LOCATION: 2
         (D) OTHER INFORMATION: /product= "OTHER"
              /note= "D-pipecolic acid"

(ix) FEATURE:
         (A) NAME/KEY: Modified-site
         (B) LOCATION: 3
         (D) OTHER INFORMATION: /product= "OTHER"
              /note= "12-aminododecanoic acid"

(ix) FEATURE:
         (A) NAME/KEY: Peptide
         (B) LOCATION: 1..15
         (D) OTHER INFORMATION: /label= P500

(xi) SEQUENCE DESCRIPTION: SEQ ID NO:36:

Arg Xaa Xaa Gly Asp Phe Glu Glu Ile Pro Glu Glu Tyr Leu Gln
1               5                  10                  15

(2) INFORMATION FOR SEQ ID NO:37:

(i) SEQUENCE CHARACTERISTICS:
         (A) LENGTH: 17 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 1
         (D) OTHER INFORMATION: /note= "dansyl group attached"

(ix) FEATURE:
         (A) NAME/KEY: Modified-site
         (B) LOCATION: 2
         (D) OTHER INFORMATION: /product= "OTHER"
             /note= "D-pipecolic acid"

(ix) FEATURE:
         (A) NAME/KEY: Modified-site
         (B) LOCATION: 3
         (D) OTHER INFORMATION: /product= "bAla"

(ix) FEATURE:
         (A) NAME/KEY: Modified-site
         (B) LOCATION: 6
         (D) OTHER INFORMATION: /product= "OTHER"
             /note= "5-aminovaleric acid"

(ix) FEATURE:
         (A) NAME/KEY: Peptide
         (B) LOCATION: 1..17
         (D) OTHER INFORMATION: /label= P498

(xi) SEQUENCE DESCRIPTION: SEQ ID NO:37:

Arg Xaa Xaa Gly Gly Xaa Asp Phe Glu Glu Ile Pro Glu Glu Tyr Leu
1               5                  10                  15

Gln (2) INFORMATION FOR SEQ ID NO:38:

(i) SEQUENCE CHARACTERISTICS:
         (A) LENGTH: 15 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 1
         (D) OTHER INFORMATION: /note= "dansyl group attached"

(ix) FEATURE:
         (A) NAME/KEY: Modified-site
         (B) LOCATION: 2
         (D) OTHER INFORMATION: /product= "OTHER"
             /note= "D-pipecolic acid"

(ix) FEATURE:
         (A) NAME/KEY: Modified-site
         (B) LOCATION: 3
         (D) OTHER INFORMATION: /product= "Acp"

(ix) FEATURE:
         (A) NAME/KEY: Modified-site
         (B) LOCATION: 4
         (D) OTHER INFORMATION: /product= "OTHER"
             /note= "12-aminododecanoic acid"

(ix) FEATURE:
              (A) NAME/KEY: Peptide
              (B) LOCATION: 1..15
              (D) OTHER INFORMATION: /label= P513

(xi) SEQUENCE DESCRIPTION: SEQ ID NO:38:

Arg Xaa Xaa Xaa Asp Phe Glu Glu Ile Pro Glu Glu Tyr Leu Gln
1               5                   10                  15

(2) INFORMATION FOR SEQ ID NO:39:

(i) SEQUENCE CHARACTERISTICS:
              (A) LENGTH: 15 amino acids
              (B) TYPE: amino acid
              (C) STRANDEDNESS: single
              (D) TOPOLOGY: linear (ix) FEATURE:
              (A) NAME/KEY: Modified-site
              (B) LOCATION: 1
              (D) OTHER INFORMATION: /note= "dansyl group attached"

(ix) FEATURE:
              (A) NAME/KEY: Modified-site
              (B) LOCATION: 2
              (D) OTHER INFORMATION: /product= "OTHER"
                  /note= "L-pipecolic acid"

(ix) FEATURE:
              (A) NAME/KEY: Modified-site
              (B) LOCATION: 3
              (D) OTHER INFORMATION: /product= "4Abu"

(ix) FEATURE:
              (A) NAME/KEY: Peptide
              (B) LOCATION: 1..15
              (D) OTHER INFORMATION: /label= P409

(xi) SEQUENCE DESCRIPTION: SEQ ID NO:39:

Arg Xaa Xaa Gly Asp Phe Glu Glu Ile Pro Glu Glu Tyr Leu Gln
1               5                   10                  15

(2) INFORMATION FOR SEQ ID NO:40:

(i) SEQUENCE CHARACTERISTICS:
              (A) LENGTH: 15 amino acids
              (B) TYPE: amino acid
              (C) STRANDEDNESS: single
              (D) TOPOLOGY: linear (ix) FEATURE:
              (A) NAME/KEY: Modified-site
              (B) LOCATION: 1
              (D) OTHER INFORMATION: /note= "dansyl group attached"

(ix) FEATURE:
              (A) NAME/KEY: Modified-site
              (B) LOCATION: 2
              (D) OTHER INFORMATION: /product= "OTHER"
                  /note= "L-pipecolic acid"

(ix) FEATURE:
              (A) NAME/KEY: Modified-site
              (B) LOCATION: 3
              (D) OTHER INFORMATION: /product= "OTHER"
                  /note= "5-aminovaleric acid"

(ix) FEATURE:
              (A) NAME/KEY: Peptide
              (B) LOCATION: 1..15
              (D) OTHER INFORMATION: /label= P547

(xi) SEQUENCE DESCRIPTION: SEQ ID NO:40:

Arg Xaa Xaa Gly Asp Phe Glu Glu Ile Pro Glu Glu Tyr Leu Gln

```
                1               5              10              15
```

(2) INFORMATION FOR SEQ ID NO:41:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "dansyl group attached"

(ix) FEATURE:
        (A) NAME/KEY: Modified-site
        (B) LOCATION: 2
        (D) OTHER INFORMATION: /product= "OTHER"
            /note= "L-pipecolic acid"

(ix) FEATURE:
        (A) NAME/KEY: Modified-site
        (B) LOCATION: 3
        (D) OTHER INFORMATION: /product= "Acp"

(ix) FEATURE:
        (A) NAME/KEY: Peptide
        (B) LOCATION: 1..15
        (D) OTHER INFORMATION: /label= P408

(xi) SEQUENCE DESCRIPTION: SEQ ID NO:41:

```
Arg Xaa Xaa Gly Asp Phe Glu Glu Ile Pro Glu Glu Tyr Leu Gln
1               5              10              15
```

(2) INFORMATION FOR SEQ ID NO:42:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "dansyl group attached"

(ix) FEATURE:
        (A) NAME/KEY: Modified-site
        (B) LOCATION: 2
        (D) OTHER INFORMATION: /product= "OTHER"
            /note= "L-pipecolic acid"

(ix) FEATURE:
        (A) NAME/KEY: Modified-site
        (B) LOCATION: 3
        (D) OTHER INFORMATION: /product= "OTHER"
            /note= "7-aminoheptanoic acid"

(ix) FEATURE:
        (A) NAME/KEY: Peptide
        (B) LOCATION: 1..15
        (D) OTHER INFORMATION: /label= P548

(xi) SEQUENCE DESCRIPTION: SEQ ID NO:42:

```
Arg Xaa Xaa Gly Asp Phe Glu Glu Ile Pro Glu Glu Tyr Leu Gln
1               5              10              15
```

(2) INFORMATION FOR SEQ ID NO:43:

(i) SEQUENCE CHARACTERISTICS:
        (A) LENGTH: 14 amino acids
        (B) TYPE: amino acid

```
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "dansyl group attached"

(ix) FEATURE:
        (A) NAME/KEY: Modified-site
        (B) LOCATION: 2
        (D) OTHER INFORMATION: /product= "OTHER"
            /note= "L-pipecolic acid"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Peptide
        (B) LOCATION: 1..14
        (D) OTHER INFORMATION: /label= P550

(xi) SEQUENCE DESCRIPTION: SEQ ID NO:43:

Arg Xaa Xaa Asp Phe Glu Glu Ile Pro Glu Glu Tyr Leu Gln
1               5                   10

(2) INFORMATION FOR SEQ ID NO:44:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "dansyl group attached"

(ix) FEATURE:
        (A) NAME/KEY: Modified-site
        (B) LOCATION: 2
        (D) OTHER INFORMATION: /product= "OTHER"
            /note= "L-pipecolic acid"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Modified-site
        (B) LOCATION: 4
        (D) OTHER INFORMATION: /product= "4Abu"

(ix) FEATURE:
        (A) NAME/KEY: Peptide
        (B) LOCATION: 1..15
        (D) OTHER INFORMATION: /label= P447

(xi) SEQUENCE DESCRIPTION: SEQ ID NO:44:

Arg Xaa Xaa Xaa Asp Phe Glu Glu Ile Pro Glu Glu Tyr Leu Gln
1               5                   10                  15

(2) INFORMATION FOR SEQ ID NO:45:

(i) SEQUENCE CHARACTERISTICS:
        (A) LENGTH: 15 amino acids
        (B) TYPE: amino acid
        (C) STRANDEDNESS: single
        (D) TOPOLOGY: linear
```

```
    (ix) FEATURE:
         (A) NAME/KEY: Modified-site
         (B) LOCATION: 1
         (D) OTHER INFORMATION: /note= "dansyl group attached"

(ix) FEATURE:
         (A) NAME/KEY: Modified-site
         (B) LOCATION: 2
         (D) OTHER INFORMATION: /product= "OTHER"
             /note= "D-pipecolic acid"

(ix) FEATURE:
         (A) NAME/KEY: Modified-site
         (B) LOCATION: 3
         (D) OTHER INFORMATION: /product= "OTHER"
             /note= "12-aminododecanoic acid"

(ix) FEATURE:
         (A) NAME/KEY: Modified-site
         (B) LOCATION: 4
         (D) OTHER INFORMATION: /product= "4Abu"

(ix) FEATURE:
         (A) NAME/KEY: Modified-site
         (B) LOCATION: 14
         (D) OTHER INFORMATION: /product= "OTHER"
             /note= "L-beta-cyclohexylalanine"

(ix) FEATURE:
         (A) NAME/KEY: Modified-site
         (B) LOCATION: 15
         (D) OTHER INFORMATION: /product= "OTHER"
             /note= "D-Glu"

(ix) FEATURE:
         (A) NAME/KEY: Peptide
         (B) LOCATION: 1..15
         (D) OTHER INFORMATION: /label= P535

(xi) SEQUENCE DESCRIPTION: SEQ ID NO:45:

Arg Xaa Xaa Xaa Asp Tyr Glu Pro Ile Pro Glu Glu Ala Xaa Xaa
1               5                   10                  15

(2) INFORMATION FOR SEQ ID NO:46:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
         (A) NAME/KEY: Modified-site
         (B) LOCATION: 1
         (D) OTHER INFORMATION: /note= "beta-naphthyl sulfonyl
             group attached"

(ix) FEATURE:
         (A) NAME/KEY: Modified-site
         (B) LOCATION: 2
         (D) OTHER INFORMATION: /product= "OTHER"
             /note= "D-pipecolic acid"

(ix) FEATURE:
         (A) NAME/KEY: Modified-site
         (B) LOCATION: 3
         (D) OTHER INFORMATION: /product= "OTHER"
             /note= "12-aminododecanoic acid"

(ix) FEATURE:
         (A) NAME/KEY: Modified-site
         (B) LOCATION: 4
         (D) OTHER INFORMATION: /product= "4Abu"

(ix) FEATURE:
         (A) NAME/KEY: Modified-site
```

(B) LOCATION: 14
                (D) OTHER INFORMATION: /product= "OTHER"
                    /note= "L-beta-cyclohexylalanine"

(ix) FEATURE:
                (A) NAME/KEY: Modified-site
                (B) LOCATION: 15
                (D) OTHER INFORMATION: /product= "OTHER"
                    /note= "D-Glu"

(ix) FEATURE:
                (A) NAME/KEY: Peptide
                (B) LOCATION: 1..15
                (D) OTHER INFORMATION: /label= P551

(xi) SEQUENCE DESCRIPTION: SEQ ID NO:46:

Arg Xaa Xaa Xaa Asp Tyr Glu Pro Ile Pro Glu Glu Ala Xaa Xaa
1               5                   10                  15

(2) INFORMATION FOR SEQ ID NO:47:

(i) SEQUENCE CHARACTERISTICS:
        (A) LENGTH: 15 amino acids
        (B) TYPE: amino acid
        (C) STRANDEDNESS: single
        (D) TOPOLOGY: linear (ix) FEATURE:
            (A) NAME/KEY: Modified-site
            (B) LOCATION: 1
            (D) OTHER INFORMATION: /note= "4-tert-butylbenzenesulfonyl
                group attached"

(ix) FEATURE:
            (A) NAME/KEY: Modified-site
            (B) LOCATION: 2
            (D) OTHER INFORMATION: /product= "OTHER"
                /note= "D-pipecolic acid"

(ix) FEATURE:
            (A) NAME/KEY: Modified-site
            (B) LOCATION: 3
            (D) OTHER INFORMATION: /product= "OTHER"
                /note= "12-aminododecanoic acid"

(ix) FEATURE:
            (A) NAME/KEY: Modified-site
            (B) LOCATION: 4
            (D) OTHER INFORMATION: /product= "4Abu"

(ix) FEATURE:
            (A) NAME/KEY: Modified-site
            (B) LOCATION: 14
            (D) OTHER INFORMATION: /product= "OTHER"
                /note= "L-beta-cyclohexylalanine"

(ix) FEATURE:
            (A) NAME/KEY: Modified-site
            (B) LOCATION: 15
            (D) OTHER INFORMATION: /product= "OTHER"
                /note= "D-Glu"

(ix) FEATURE:
            (A) NAME/KEY: Peptide
            (B) LOCATION: 1..15
            (D) OTHER INFORMATION: /label= P553

(xi) SEQUENCE DESCRIPTION: SEQ ID NO:47:

Arg Xaa Xaa Xaa Asp Tyr Glu Pro Ile Pro Glu Glu Ala Xaa Xaa
1               5                   10                  15

(2) INFORMATION FOR SEQ ID NO:48:

(i) SEQUENCE CHARACTERISTICS:
        (A) LENGTH: 15 amino acids

```
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "alpha-naphthyl sulfonyl
            group attached"

(ix) FEATURE:
        (A) NAME/KEY: Modified-site
        (B) LOCATION: 2
        (D) OTHER INFORMATION: /product= "OTHER"
            /note= "D-pipecolic acid"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Modified-site
        (B) LOCATION: 4
        (D) OTHER INFORMATION: /product= "4Abu"

(ix) FEATURE:
        (A) NAME/KEY: Modified-site
        (B) LOCATION: 14
        (D) OTHER INFORMATION: /product= "OTHER"
            /note= "L-beta-cyclohexylalanine"

(ix) FEATURE:
        (A) NAME/KEY: Modified-site
        (B) LOCATION: 15
        (D) OTHER INFORMATION: /product= "OTHER"
            /note= "D-Glu"

(ix) FEATURE:
        (A) NAME/KEY: Peptide
        (B) LOCATION: 1..15
        (D) OTHER INFORMATION: /label= P581

(xi) SEQUENCE DESCRIPTION: SEQ ID NO:48:

Arg Xaa Xaa Xaa Asp Tyr Glu Pro Ile Pro Glu Glu Ala Xaa Xaa
1               5                   10                  15

(2) INFORMATION FOR SEQ ID NO:49:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "tert-butylbenzenesulfonyl
            group attached"

(ix) FEATURE:
        (A) NAME/KEY: Modified-site
        (B) LOCATION: 2
        (D) OTHER INFORMATION: /product= "OTHER"
            /note= "D-pipecolic acid"

(ix) FEATURE:
        (A) NAME/KEY: Modified-site
        (B) LOCATION: 3
        (D) OTHER INFORMATION: /product= "OTHER"
            /note= "12-aminododecanoic acid"

(ix) FEATURE:
        (A) NAME/KEY: Modified-site
        (B) LOCATION: 4
```

```
              (D) OTHER INFORMATION: /product= "4Abu"

(ix) FEATURE:
              (A) NAME/KEY: Peptide
              (B) LOCATION: 1..11
              (D) OTHER INFORMATION: /label= BCH-2443

(xi) SEQUENCE DESCRIPTION: SEQ ID NO:49:

Arg Xaa Xaa Xaa Asp Phe Glu Pro Ile Pro Tyr
1               5                  10

(2) INFORMATION FOR SEQ ID NO:50:

(i) SEQUENCE CHARACTERISTICS:
              (A) LENGTH: 11 amino acids
              (B) TYPE: amino acid
              (C) STRANDEDNESS: single
              (D) TOPOLOGY: linear (ix) FEATURE:
              (A) NAME/KEY: Modified-site
              (B) LOCATION: 1
              (D) OTHER INFORMATION: /note= "tert-butylbenzenesulfonyl
                   group attached"

(ix) FEATURE:
              (A) NAME/KEY: Modified-site
              (B) LOCATION: 2
              (D) OTHER INFORMATION: /product= "OTHER"
                   /note= "D-pipecolic acid"

(ix) FEATURE:
              (A) NAME/KEY: Modified-site
              (B) LOCATION: 3
              (D) OTHER INFORMATION: /product= "OTHER"
                   /note= "12-aminododecanoic acid"

(ix) FEATURE:
              (A) NAME/KEY: Modified-site
              (B) LOCATION: 4
              (D) OTHER INFORMATION: /product= "4Abu"

(ix) FEATURE:
              (A) NAME/KEY: Peptide
              (B) LOCATION: 1..11
              (D) OTHER INFORMATION: /label= BCH-2736

(xi) SEQUENCE DESCRIPTION: SEQ ID NO:50:

Arg Xaa Xaa Xaa Asp Phe Glu Pro Ile Pro Tyr
1               5                  10

(2) INFORMATION FOR SEQ ID NO:51:

(i) SEQUENCE CHARACTERISTICS:
              (A) LENGTH: 11 amino acids
              (B) TYPE: amino acid
              (C) STRANDEDNESS: single
              (D) TOPOLOGY: linear (ix) FEATURE:
              (A) NAME/KEY: Modified-site
              (B) LOCATION: 1
              (D) OTHER INFORMATION: /note= "tert-butylbenzenesulfonyl
                   group attached"

(ix) FEATURE:
              (A) NAME/KEY: Modified-site
              (B) LOCATION: 2
              (D) OTHER INFORMATION: /product= "OTHER"
                   /note= "D-pipecolic acid"

(ix) FEATURE:
              (A) NAME/KEY: Modified-site
              (B) LOCATION: 3
              (D) OTHER INFORMATION: /product= "OTHER"
```

/note= "12-aminododecanoic acid"

(ix) FEATURE:
             (A) NAME/KEY: Modified-site
             (B) LOCATION: 4
             (D) OTHER INFORMATION: /product= "4Abu"

(ix) FEATURE:
             (A) NAME/KEY: Peptide
             (B) LOCATION: 1..11
             (D) OTHER INFORMATION: /label= BCH-2741

(xi) SEQUENCE DESCRIPTION: SEQ ID NO:51:

Arg Xaa Xaa Xaa Asp Phe Glu Pro Ile Pro Tyr
1               5                   10

(2) INFORMATION FOR SEQ ID NO:52:

(i) SEQUENCE CHARACTERISTICS:
             (A) LENGTH: 11 amino acids
             (B) TYPE: amino acid
             (C) STRANDEDNESS: single
             (D) TOPOLOGY: linear (ix) FEATURE:
             (A) NAME/KEY: Modified-site
             (B) LOCATION: 1
             (D) OTHER INFORMATION: /note= "4-bromobenzenesulfonyl
                    group attached"

(ix) FEATURE:
             (A) NAME/KEY: Modified-site
             (B) LOCATION: 2
             (D) OTHER INFORMATION: /product= "OTHER"
                    /note= "D-pipecolic acid"

(ix) FEATURE:
             (A) NAME/KEY: Modified-site
             (B) LOCATION: 3
             (D) OTHER INFORMATION: /product= "OTHER"
                    /note= "12-aminododecanoic acid"

(ix) FEATURE:
             (A) NAME/KEY: Modified-site
             (B) LOCATION: 4
             (D) OTHER INFORMATION: /product= "4Abu"

(ix) FEATURE:
             (A) NAME/KEY: Peptide
             (B) LOCATION: 1..11
             (D) OTHER INFORMATION: /label= BCH-2733

(xi) SEQUENCE DESCRIPTION: SEQ ID NO:52:

Arg Xaa Xaa Xaa Asp Phe Glu Pro Ile Pro Tyr
1               5                   10

(2) INFORMATION FOR SEQ ID NO:53:

(i) SEQUENCE CHARACTERISTICS:
             (A) LENGTH: 11 amino acids
             (B) TYPE: amino acid
             (C) STRANDEDNESS: single
             (D) TOPOLOGY: linear (ix) FEATURE:
             (A) NAME/KEY: Modified-site
             (B) LOCATION: 1
             (D) OTHER INFORMATION: /note=
                    "2,4,6-triisopropylbenzensulfonyl group attached"

(ix) FEATURE:
             (A) NAME/KEY: Modified-site
             (B) LOCATION: 2
             (D) OTHER INFORMATION: /product= "OTHER"
                    /note= "D-pipecolic acid"

```
      (ix) FEATURE:
           (A) NAME/KEY: Modified-site
           (B) LOCATION: 3
           (D) OTHER INFORMATION: /product= "OTHER"
               /note= "12-aminododecanoic acid"

(ix) FEATURE:
           (A) NAME/KEY: Modified-site
           (B) LOCATION: 4
           (D) OTHER INFORMATION: /product= "4Abu"

(ix) FEATURE:
           (A) NAME/KEY: Peptide
           (B) LOCATION: 1..11
           (D) OTHER INFORMATION: /label= BCH-2444

(xi) SEQUENCE DESCRIPTION: SEQ ID NO:53:

Arg Xaa Xaa Xaa Asp Phe Glu Pro Ile Pro Tyr
1               5                   10

(2) INFORMATION FOR SEQ ID NO:54:

(i) SEQUENCE CHARACTERISTICS:
         (A) LENGTH: 4 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 1
         (D) OTHER INFORMATION: /product= "bAla"

(ix) FEATURE:
         (A) NAME/KEY: Modified-site
         (B) LOCATION: 4
         (D) OTHER INFORMATION: /product= "OTHER"
             /note= "gamma-aminovaleric acid"

(xi) SEQUENCE DESCRIPTION: SEQ ID NO:54:

Xaa Gly Gly Xaa
1

(2) INFORMATION FOR SEQ ID NO:55:

(i) SEQUENCE CHARACTERISTICS:
         (A) LENGTH: 11 amino acids
         (B) TYPE: amino acid
         (C) STRANDEDNESS: single
         (D) TOPOLOGY: linear (xi) SEQUENCE DESCRIPTION: SEQ ID NO:55:

Asp Phe Glu Glu Ile Pro Glu Glu Tyr Leu Gln
     1               5                   10

(2) INFORMATION FOR SEQ ID NO:56:

(i) SEQUENCE CHARACTERISTICS:
         (A) LENGTH: 11 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 10
         (D) OTHER INFORMATION: /product= "OTHER"
             /note= "L-beta-cyclohexylalanine"

(ix) FEATURE:
         (A) NAME/KEY: Modified-site
         (B) LOCATION: 11
```

```
         (D) OTHER INFORMATION: /product= "OTHER"
             /note= "D-Glu"

(xi) SEQUENCE DESCRIPTION: SEQ ID NO:56:

Asp Tyr Glu Pro Ile Pro Glu Glu Ala Xaa Xaa
1               5                   10

(2) INFORMATION FOR SEQ ID NO:57:

(i) SEQUENCE CHARACTERISTICS:
       (A) LENGTH: 7 amino acids
       (B) TYPE: amino acid
       (C) STRANDEDNESS: single
       (D) TOPOLOGY: linear (xi) SEQUENCE DESCRIPTION: SEQ ID NO:57:

Asp Phe Glu Pro Ile Pro Tyr
1               5
```